(12) United States Patent
Shalaby et al.

(10) Patent No.: US 8,085,987 B2
(45) Date of Patent: Dec. 27, 2011

(54) METHOD AND TOOL FOR SURFACE TEXTURE EVALUATION

(76) Inventors: Ahmed Shalaby, Winnipeg (CA); Amin El Gendy, Winnipeg (CA)

( * ) Notice: Subject to any disclaimer, the term of this patent is extended or adjusted under 35 U.S.C. 154(b) by 671 days.

(21) Appl. No.: 12/257,911

(22) Filed: Oct. 24, 2008

(65) Prior Publication Data

US 2009/0116697 A1 May 7, 2009

Related U.S. Application Data

(60) Provisional application No. 60/982,838, filed on Oct. 26, 2007.

(51) Int. Cl.
G06K 9/00 (2006.01)
G01C 3/08 (2006.01)
(52) U.S. Cl. ....... 382/108; 356/4.01; 356/5.15; 382/106
(58) Field of Classification Search .......... 382/108, 382/166, 128, 224, 133, 110; 356/4.01, 5.01, 356/5.1, 5.15, 28; 342/70–72; 348/43, 46, 348/54, 57, 254, 58
See application file for complete search history.

(56) References Cited

U.S. PATENT DOCUMENTS

| 7,742,169 | B2* | 6/2010 | Morita | 356/369 |
| 7,948,514 | B2* | 5/2011 | Sato et al. | 348/46 |
| 7,973,911 | B2* | 7/2011 | Takahashi | 356/4.01 |
| 2006/0018514 | A1* | 1/2006 | Bankhead | 382/108 |
| 2007/0222781 | A1* | 9/2007 | Kondo et al. | 345/426 |

OTHER PUBLICATIONS

Barsky et al (The 4-Source photometric stereo Technique for three dimensional surfaces in the presence of highlights and shadows), Oct. 2003.*

Bringier et al (Photometric reconstruction of a dynamic textured surface from just one color image acquiaition), Mar. 2008.*

* cited by examiner

*Primary Examiner* — Vikkram Bali
*Assistant Examiner* — Nancy Bitar
(74) *Attorney, Agent, or Firm* — Ryan W. Dupuis; Kyle R. Satterthwaite; Ade & Company Inc

(57) ABSTRACT

Texture of a surface, for example concrete, is evaluated by capturing images of the surface facing the surface in a direction of an orthogonal axis extending perpendicularly from the surface while sequentially projecting light onto the surface from each of four light source positions spaced circumferentially about the orthogonal axis. A specularity condition is determined to exist in one of the four images by comparing intensities of the images directly with one another. If a specularity condition exists, three images of the four images which are least affected by specularity are used to determining a surface gradient of the surface.

20 Claims, 28 Drawing Sheets a) Perspective Projection b) Orthographic Projection a) A baseboard is used to adjust the height of the template b) Calibrating light direction using shadow of a nail a) Diffuse surface  b) Specular surface a) Diffuse object  b) $(i_0(x,y) + i_{180}(x,y)) > (i_{90}(x,y) + i_{270}(x,y)) + i_{thr}$  c) $i_0(x,y) > i_{180}(x,y)$ d) Specular object  e) $(i_0(x,y) + i_{180}(x,y)) > (i_{90}(x,y) + i_{270}(x,y)) + i_{thr}$  f) $i_0(x,y) > i_{180}(x,y)$ a) Measured profile before filtering b) Band-pass filtered profile after removing wavelengths ≥ 100 mm and wavelengths ≤ 2.5 mm c) Computed MPD for a sample baseline length of 100 mm a) Part of Sample E1 b) Global integration c) Local integration a) Recovered surface c) Sample E1 b) Power Spectrum of the recovered surface

Table 8-1 Pavement sample properties

| Sample | RMS (mm) | MPD (mm) | Description |
|---|---|---|---|
| A1 | 0.14 | 0.42 | Concrete. Side walk with smooth surface. |
| B1 | 0.61 | 1.31 | Asphalt pavement. Worn out surface. |
| B2 | 0.69 | 1.67 | |
| C1 | 0.59 | 2.09 | Asphalt pavement. Polished surface. |
| C2 | 0.75 | 2.38 | |
| D1 | 0.87 | 2.70 | Asphalt pavement. Moderate polished and worn surface. |
| D2 | 1.01 | 2.81 | |
| E1 | 1.11 | 3.43 | Asphalt pavement. Harsh surface. |
| E2 | 1.21 | 3.76 | |

FIG 39

METHOD AND TOOL FOR SURFACE TEXTURE EVALUATION

The present application claims benefit under 35 USC Section 119(e) of U.S. Provisional Patent Application Ser. No. 60/982,838 filed on Oct. 26, 2007. The present application is based on and claims priority from this application, the disclosure of which is expressly incorporated herein by reference.

FIELD OF THE INVENTION

The present invention relates to a method of evaluating texture of a surface using a photometric stereo technique in which a specularity condition can be determined and corrected for, and further relates to a tool for executing the method according to the present invention.

BACKGROUND

Characterization of pavement surface texture is important for pavement management applications. Surface texture can affect road characteristics and vehicle performance in the areas of tire wear, rolling resistance, tire/road friction, noise in vehicles, exterior road noise, discomfort and wear in vehicles (ISO 13473-1 1997). Pavement macro- and micro-texture have significant impacts on skid resistance and generated noise.

Many of the pavement texture measurement devices reduce the data to a single attribute such as mean profile depth or hydraulic radius. Texture size, spacing, and distribution should also be considered. Therefore, advanced methods that characterize pavement texture in three dimensions are needed.

Photometric stereo technique is an example of a technique for characterizing texture of a surface in three dimensions. Specularity is an important consideration when using photometric stereo technique; therefore, different algorithms have been introduced to recover the shape of specular surfaces. Coleman and Jain [1], proposed a method to detect specularity component from four-source stereo technique by calculating four surface reflectance factors, one for each three-source combination. The deviation of the calculated reflectance factors is tested against a threshold value. If specularity exists, the combination of the photos that gives the smallest reflectance factor will be used to compute the surface normals. Ikeuchi [2] used a linear light source to study specular surfaces.

In the prior art according to Coleman and Jain a photometric stereo technique is applied for multiple light sources but which requires a complex calculation to determine if there is specularity in the images captured such that the resulting algorithm is slow and cumbersome, while unsatisfactorily overcoming errors due to specularity.

SUMMARY OF THE INVENTION

According to one aspect of the invention there is provided a method of evaluating texture of a surface, the method comprising:

providing an image capturing device arranged to capture an image;

providing a source of light arranged to project light in a lighting direction;

locating the image capturing device along an orthogonal axis extending perpendicularly from the surface and facing the surface in a direction of the orthogonal axis so as to be arranged to capture an image of the surface;

sequentially projecting light onto the surface from each of four light source positions spaced circumferentially about the orthogonal axis;

arranging the lighting direction to be at a constant angle of inclination relative to the orthogonal axis in each of the four light source positions;

arranging an intensity of the projected light to be constant in each of the four light source positions;

capturing four images of the surface using the image capturing device in which the surface is illuminated by the light source from a respective one of the four lighting positions when each of the four images are captured;

determining if a specularity condition exists in one of the four images by comparing intensities of the images directly with one another;

if a specularity condition exists:
i) determining three images of the four images which are least affected by specularity; and
ii) determining a surface gradient of the surface using the three images.

By directly comparing intensity values of the captured images, fewer calculations are required to be performed so that the resulting algorithm for determining if specularity is present is much more efficient and easy to implement. Furthermore by arranging images to capture lighting from diametrically opposed directions, comparison between intensities can be accomplished directly with a simplified algorithm and with improved accuracy in detecting specularity errors.

Preferably the method includes arranging the four light source positions to comprise two pairs of diametrically opposed positions and determining if a specularity condition exists by calculating a difference between a summation of intensities of the images of one of the pairs of light source positions and a summation of intensities of the images of the other pair of light source positions and comparing the difference to a prescribed threshold comprising approximately 20% of a magnitude of the values being compared.

Alternatively, if no specularity condition exists, the surface gradient of the surface can be determined using all four of the images.

Three images of the four images which are least affected by specularity are preferably determined by excluding the image having the greatest intensity among the images of one pair of lighting positions having the greatest sum of intensity.

According to a further aspect of the present invention there is provided a method of evaluating texture of a surface, the method comprising:

providing an image capturing device arranged to capture an image;

providing a source of light arranged to project light in a lighting direction;

locating the image capturing device along an orthogonal axis extending perpendicularly from the surface and facing the surface in a direction of the orthogonal axis so as to be arranged to capture an image of the surface;

sequentially projecting light onto the surface from each of four light source positions spaced circumferentially about the orthogonal axis;

arranging the lighting direction to be at a constant angle of inclination relative to the orthogonal axis in each of the four light source positions;

arranging an intensity of the projected light to be constant in each of the four light source positions;

capturing four images of the surface using the image capturing device in which the surface is illuminated by the light source from a respective one of the four lighting positions when each of the four images are captured;

determining if a shadow condition exists in one of the four images by comparing intensities of the images to a prescribed threshold;
if a shadow condition exists:
i) determining three images of the four images which are least affected by shadow; and
ii) determining a surface gradient of the surface using the three images.

This method may further include arranging the prescribed threshold to comprise a percentage of a maximum intensity among the intensities of the images, for example 4% of the maximum intensity among the images, and determining if the shadow condition exists if intensity of one of the images is less than the prescribed threshold.

If no shadow condition or specularity condition exists, the method includes determining a surface gradient of the surface using all four of the images.

When determining the surface gradient using three images of the four images which are least affected by shadow, the image having lowest intensity is excluded.

According to another aspect of the present invention there is provided a tool for evaluating texture of a surface, the tool comprising:
a housing including a bottom end arranged to receive the surface;
an image capturing device arranged to capture an image;
the image capturing device being supported on the housing along an orthogonal axis extending perpendicularly from a plane of the bottom end and facing the bottom end in a direction of the orthogonal axis so as to be arranged to capture an image of the surface at the bottom end;
a source of light arranged to project light;
the source of light being supported on the housing so as to project light from any one of four light source positions spaced circumferentially about the orthogonal axis;
the source of light being arranged to project light from each of the four light source positions towards the bottom end at a constant angle of inclination relative to the orthogonal axis;
the source of light being arranged to be constant in intensity from each of the four light source positions;
a controller arranged to actuate the image capturing device to capture one image when light is projected at the bottom end from each one of the four light source positions; and
a processor arranged to determine if a specularity condition exists in one of the four images by comparing intensities of the images directly with one another,
the processor being further arranged, if a specularity condition exists, to:
i) determine three images of the four images which are least affected by specularity; and
ii) determine a surface gradient of the surface using the three images.

According to yet another aspect of the present invention there is provided a tool for evaluating texture of a surface, the tool comprising:
a housing including a bottom end arranged to receive the surface;
an image capturing device arranged to capture an image;
the image capturing device being supported on the housing along an orthogonal axis extending perpendicularly from a plane of the bottom end and facing the bottom end in a direction of the orthogonal axis so as to be arranged to capture an image of the surface at the bottom end;
a source of light arranged to project light;
the source of light being supported on the housing so as to project light from any one of four light source positions spaced circumferentially about the orthogonal axis;
the source of light being arranged to project light from each of the four light source positions towards the bottom end at a constant angle of inclination relative to the orthogonal axis;
the source of light being arranged to be constant in intensity from each of the four light source positions;
a controller arranged to actuate the image capturing device to capture one image when light is projected at the bottom end from each one of the four light source positions; and
a processor arranged to determine if a shadow condition exists in one of the four images by comparing intensities of the images to a prescribed threshold, the processor being further arranged, if a shadow condition exists, to:
i) determine three images of the four images which are least affected by shadow; and
ii) determine a surface gradient of the surface using the three images.

Some embodiments of the invention will now be described in conjunction with the accompanying drawings in which:

BRIEF DESCRIPTION OF THE DRAWINGS

FIG. 39 is a table comparing properties of several different pavement samples In the drawings like characters of reference indicate corresponding parts in the different figures.

DETAILED DESCRIPTION

Figure 1:
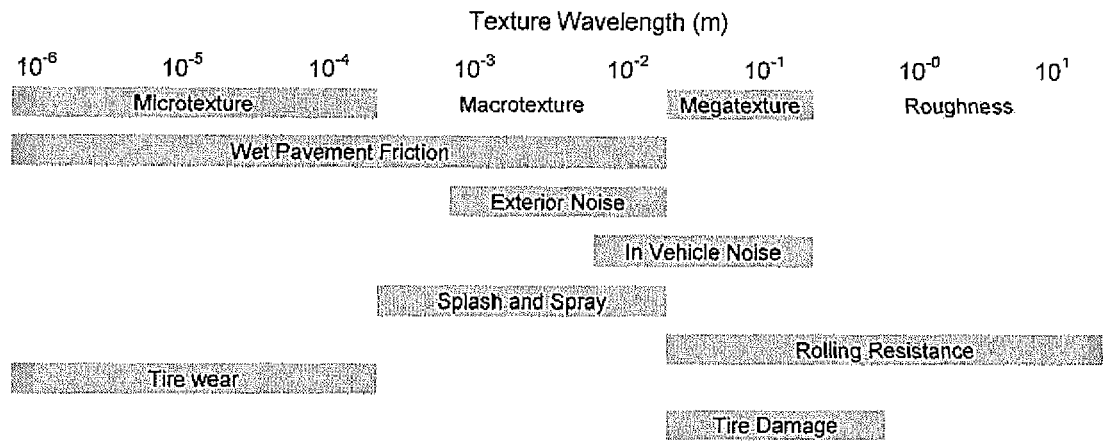
FIG. 1 is a schematic illustration of ranges in terms of texture wavelength and their most significant effects (ISO 13473-1).

The present invention is generally concerned with the recovery of pavement surface texture using photometric stereo techniques. A prototype of four-source photometric stereo system is presented. On the basis of the advantage of the four light sources, a new algorithm for detecting specular and shadow effects is introduced. The algorithm also computes such surface texture indicators as mean profile depth.

The ability of the proposed system is assessed by testing synthetic and real surfaces. A known dimensional sphere with/without specular surface is tested to validate the algorithm for detecting specularity.

Five types of pavement surfaces are tested to demonstrate the ability of the system to recover the real three-dimensional pavement surface. For each sample, six profiles are measured manually by using a depth dial gauge. Surface characteristics extracted from manually measured profiles are compared with those computed using the photometric stereo system in which surface heights are recovered by using both global and local integration methods.

The three-dimensional surface heights are recovered under different illumination angles to determine the optimal zenith angle ($\sigma$). Five zenith angles, $\sigma$=26°, 28°, 30°, 33°, and 34°, are examined. For each zenith angle, the photometric stereo system is calibrated Test results show that pavement surface texture estimated by global integration method is more accurate than those estimated by local integration method. Also results show that $\sigma$=30° is the optimal zenith angle ($\sigma$).

The information that the system can provide is extended by using a two dimensional Fourier transform of the recovered surface. Energy computed from the power spectrum of the two dimensional Fourier transform of the recovered surface is introduced as a new texture indicator. Analyzing surface texture in frequency domain is chosen for two reasons: a) the image-based surface is already recovered in the frequency domain; b) texture surface can be filtered so that only the frequencies of interest are considered. The mean profile depth and mean square roughness are correlated with the frequency domain indicator. The analysis shows that energy of the power spectrum can be used to classify pavement texture, and it is a good predictor of the mean profile depth and root mean square roughness.

Finally, a plan for estimating slipping friction coefficient of the pavement surface is introduced.

The present invention introduces a method for measuring pavement surface texture. Current measurement devices provide a single attribute from the two-dimensional profile e.g. mean profile depth and mean square roughness. The thesis objective is to introduce a new method to reconstruct the three-dimensional shape of the pavement surface texture.

Our aim is to develop a prototype of four-source photometric stereo system for recovering pavement surface shape. A new four-source photometric stereo approach to detect specularity and shadow contributions is presented.

Different types of pavement surface textures are tested to assess the proposed system. For each sample, six profiles are measured manually by using a depth dial gauge. Surface texture indicators such as mean profile depth and root mean square roughness are compared with those indicators computed from surfaces recovered by using the photometric stereo system. Surface heights are recovered by using both global and local integration methods.

The three-dimensional surface heights are recovered under different illumination angles to determine the optimal zenith angle ($\sigma$). Five zenith angles, $\sigma$=26°, 28°, 30°, 33°, and 34°, are examined. For each zenith angle, the photometric stereo system is calibrated and adjusted by using a printed template. An angle alignment board is used to verify the vertical and horizontal illumination directions.

Finally, a new surface texture indicator computed from the power spectrum energy of the Fourier transform of the surface height is presented. Two models to estimate the mean profile depth and the root mean square roughness from the power spectrum indicator is discussed.

Macrotexture and Microtexture of Road Surface

Introduction

Characterization of pavement surface texture is important for pavement management applications. As shown in FIG. 1, surface texture affects road characteristics and vehicle performance in the areas of tire wear, rolling resistance, tire and road friction, noise in vehicles, exterior road noise, discomfort, and wear in vehicles (ISO 13473-1 1997).

Pavement macrotexture and microtexture have significant impacts on skid resistance and generated noise. A number of studies linked friction with surface texture. Britton et al. (1974) studied the influence of texture on tire/road friction. Skid numbers are governed by three macrotexture parameters and three microtexture parameters, which can be expressed in terms of texture size, spacing or distribution, and shape. Ergun et al. (2005) developed a friction-coefficient prediction model that is based on microtexture profiles measured by using an image analysis technique. The surface profile was recovered by projecting the light source on a razor blade placed above the surface. The shadow of the blade on the sample reveals the surface profile. By accumulating surface profiles, the surface is recovered, and hence the parameters that correlate texture with friction are computed. The study found that the average wavelength of the profile is the most is the most reliable texture parameter that can predict the friction coefficient at no slipping.

Texture was also linked to noise in a number of studies. Balmer (1978) discussed the influence of pavement surface texture on skid resistance, on the accident rate on wet pavement, on pavement wear, and on noise generated by tire/road interaction. Balmer found that the noise produced by tire/road interaction increases with pavement texture depth. Klein et al. (2004) presented an envelopment procedure that correlated texture profiles with noise levels in the frequency domain. Inoue and Ihara (2004) studied the effect of surface texture of porous asphalt on tire/road noise reduction. Surface texture indexes such as mean texture depth, mean profile depth, standard deviation of surface profile, and ratio of accumulated length of 2 mm texture depth (RAL2) were examined. RAL2 was found as an effective index on tire/road noise reduction.

This chapter discusses road texture classifications, definitions of terms used to quantify texture, and different devices used for measuring macrotexture.

Basic Terms Describing Texture

Pavement texture is defined as the deviation of a pavement surface from a true surface within a specified wavelength range. As shown in Table 2-1, four ranges of texture are based on wavelengths: microtexture, macrotexture, megatexture, and unevenness (ASTM E1845 2005 and ISO 13473-1 1997).

TABLE 2-1

Texture classifications

| Texture Classification | Relative Wavelengths |
|---|---|
| Microtexture | $\lambda \leq 0.5$ mm |
| Macrotexture | $0.5$ mm $\leq \lambda \leq 50$ mm |
| Megatexture | $50$ mm $\leq \lambda \leq 500$ mm |
| Unevenness (Roughness) | $0.5$ m $\leq \lambda \leq 50$ m |

Figure 2:
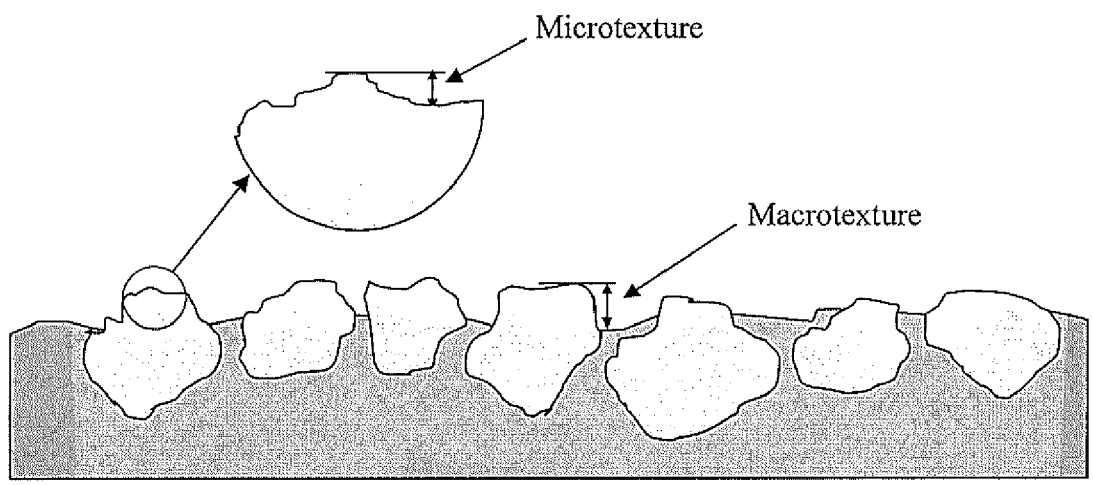
FIG. 2 is a schematic representation of macrotexture and microtexture.

Microtexture describes pavement surface deviations with wavelength less than 0.5 mm. It is texture on the microscopic level which is too small to be observed by the eye. Microtexture is formed by either fine aggregate particles (sand) or surface roughness of the large aggregate. The concept of pavement macrotexture and microtexture is illustrated in FIG. 2 (Flintsch et al. 2003).

Macrotexture is formed by large aggregate and its wavelengths are between 0.5 and 50 mm which is the same order of size as coarse aggregate or tire tread elements. To enhance pavement skid resistance, macrotexture may be formed artificially by cutting or sawing of the concrete surface. The American Concrete Pavement Association (2000) described different methods to produce artificial texture that could improve pavement skid resistance.

Megatexture has wavelengths between 50 to 500 mm which is the same order of size as tire/road contact area.

Unevenness surface, a type of surface roughness which affects the ride comfort, has wavelengths longer than 0.5 m.

Figure 3:
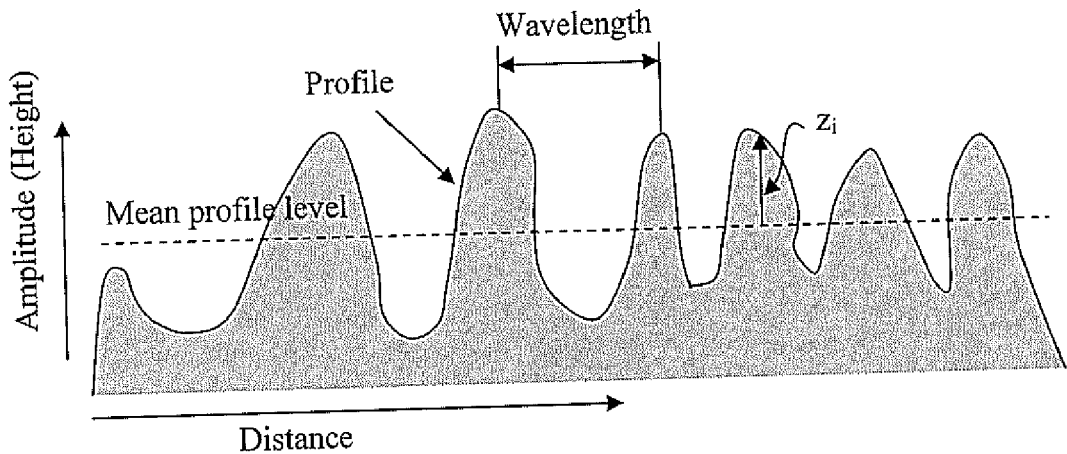
FIG. 3 is an elevational view of a pavement surface profile.

FIG. 3 shows a typical profile of pavement surface included basic terms used to define profile (Bennett and Mattsson 1999, ISO 4287 1997, and ISO 13473-1 1997). The root mean square deviation or roughness (rms roughness) is the standard deviation of the height of the surface.

For a single profile, the root mean square roughness δ is calculated as:

$$\delta = \sqrt{\frac{1}{n}\sum_{i=1}^{n} z_i^2} \qquad (2.1)$$

where
$z_i$=height of surface profile from the mean profile level at position i,
n=number of discrete measured points along the profile length.

Texture Depth

Texture depth is defined within a surface area as that of a tire/pavement interface in the three-dimensional case, or within a distance as that of a tire/pavement interface in the two dimensional case as follows (ISO 13473-1 1997):

Texture Depth, TD: The vertical distance between the surface and plane through the top of the three highest peaks of the surface.

Mean Texture Depth, MTD: The average pavement macrotexture depth measured using the volumetric patch method. See section 2.4.1

Profile Depth, PD: The vertical distance between the profile and a horizontal line through the top of the highest peak of the profile.

Mean Profile Depth, MPD: The average pavement macrotexture depth measured over the length of the profile, in the two dimensional case, which is called baseline and always 100 mm length as described in detail in section 2.4.2.

Estimated Texture Depth, ETD: Term used to estimate the mean texture depth from the mean profile depth. The Estimated Texture Depth (ETD) is calculated from the MPD by the following formula:

$$ETD=0.8MPD+0.2mm \qquad (2.2)$$

where ETD and MPD are expressed in millimetres.

Measuring Pavement Surface Texture

Flintsch et al. (2003) discussed various techniques for measuring pavement macrotexture and their applications. The two main classes of techniques are static and dynamic.

In pavement management applications, microtexture is not measured directly in the field. However microtexture effects can be detected from skid resistance measurements. Leu and Henry (1978) developed a model that correlates low-speed skid with the measurements of pavement macrotexture and microtexture. Available devices for low-speed skid resistance measurement include the British Portable Tester (BPT) (ASTM E303-93 2005), and the Dynamic Friction Tester (DF Tester) (ASTM E1911-98 2005).

Since the thesis proposed technique is static, such static macrotexture techniques as the volumetric patch method, the outflow meter, and the circular texture meter are described in the following section.

The Volumetric Patch Method

The volumetric patch method, ASTM E965-96 (2005), or sand patch method is a technique for measuring the average depth of pavement surface macrotexture by spreading a predetermined volume of material and measuring the covered area. The mean texture depth of pavement macrotexture is calculated by the following equation:

$$MTD = \frac{4V}{\pi D^2} \quad (2.3)$$

where:
V=sample volume, and
D=average diameter of the area covered by the material.

The material previously used in this test was sand. Now, for better results, sand particles are replaced with solid rounded glass spheres. The volumetric patch test is considered crude and slow; however, it is widely used as a benchmark for other techniques (ASTM E965-96 2005).

Measuring Mean Profile Depth

Many techniques have been developed to overcome the limitations of the volumetric patch method. With the growth of the number of new techniques, a standard method for computing the average depth of the pavement surface macrotexture from the surface profile was established (ASTM E1845 2005 and ISO 13473-1 1997). The objective of this standard is to make the macrotexture measurements interchangeable between techniques by correlating them with the mean texture depth obtained by the volumetric patch method.

The surface profile must be filtered before computing the mean profile depth (MPD). There are two alternative methods for filtering:

Applying a high-pass filter to remove wavelengths≧100 mm followed by applying a low-pass filter to remove wavelengths≦2.5 mm; and Applying a low-pass filter to remove wavelengths≦2.5 mm, followed by suppressing profile slope by subtracting a regression line from the profile.

Figure 4:
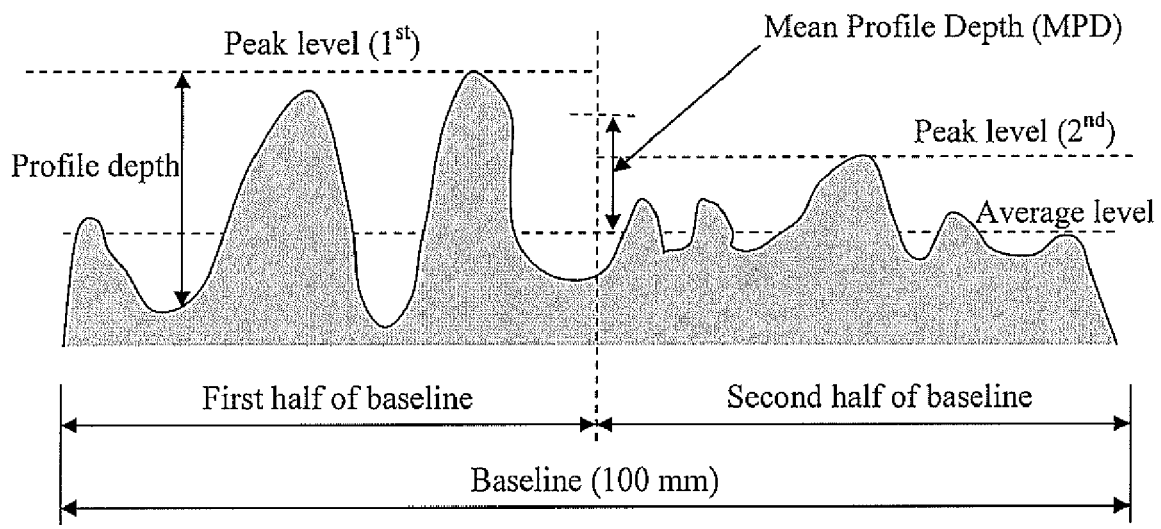
FIG. 4 is a elevational representation of a mean profile depth computation (ISO 13473-1 1997).

The mean profile depth is computed from a sample baseline length of 100 mm, which is divided into two equal halves, as shown in FIG. 4. The peak level of each half is detected, and the difference between the average of the two peaks and the profile average is termed the MPD. The test is repeated for different profiles, and the average is reported as MPD of the sample.

The Outflow Meter

The Outflow Meter, ASTM E2380-05 (2005), measures the required time for a fixed volume of water to escape from a specified cylinder with a rubber bottom through voids in the pavement texture. Measured time is related to both the mean hydraulic radius of paved surface and the mean texture depth. This test is suitable for evaluating the surface drainage or the internal drainage of the surface course of a pavement.

For each pavement test section, a minimum of four randomly spaced tests are required. All outflow meter test times are averaged and reported. The estimated mean texture depth is calculated as follows:

$$MTD=3.114/OFT+0.636 \quad (2.4)$$

where OFT is the average of all outflow meter test times recorded to the 0.01 second.

The Circular Track Meter

The Circular Track Meter, CTMeter (ASTM E2157 2005 and Abe et al. 2001), measures macrotexture properties by using a laser-displacement sensor mounted on an arm that rotates on a circular track with a 284 mm diameter. The profile data are sampled at intervals of approximately 0.9 mm divided into eight segments. The mean profile depths from the eight segments are averaged and reported as the mean profile depth MPD of the sample. The mean texture depth is estimated from the MPD by the CTMeter according to the following equation:

$$MTD=0.947MPD+0.069\text{mm} \quad (2.5)$$

where MTD and MPD are expressed in millimetres.

Image Processing Applications and Pavement Management

Introduction

Image processing techniques are now widely applied in monitoring pavement conditions. With the progress in image processing technology, different techniques are used for extracting pavement information from images. In this chapter, a literature review of image processing applications that recently used in pavement management is introduced. The review shows that using photometric stereo to recover pavement surface height is a new area of image processing application in pavement management.

Image Processing Applications

Images of surface pavement were used by Schonfeld (1970) for documenting pavement conditions. Schonfeld used stereophotographs for describing pavement surface texture in terms of seven texture parameters. Texture images were viewed through a microstereoscope and also through a standard stereoscope. The pavement surface was analyzed into texture elements based on a table of defined texture parameters.

Hryciw and Raschke (1996) characterized soil in situ using two phases of image processing techniques. In the first phase, grain size distribution of subsurface was computed from images. A cut-off greyscale value (threshold) separating the particles from background was used to segment images. A predetermined intensity for background was used (white background) so that other image intensities belong to soil particles. Each of the foreground regions represents soil particle. In second phase, images were analyzed in the frequency domain. The two-dimensional Fourier transform of the image was used to characterize the texture according to the Fourier power spectrum. Coarse texture has a large spatial period with spectral energy concentrated at low frequencies.

Masad et al. (2000) and Masad et al. (2001) used the same technique to find aggregate shape indexes (e.g. angularity and texture). They examined the correlation between fine aggregate shape indexes and asphalt mixture performance.

Kuo et al. (1996) measured length, breadth, and convex area of aggregate particles using two images of each sample. They attached aggregate particles in sample trays with two perpendicular faces. The sample tray was rotated 90 degrees. Two images were taken to the sample before and after rotating the tray. Images provided three-dimensional information about particles. The system provided shape indexes driven from area and perimeter length.

Instead of rotating sample trays, Rao and Tutumluer (2000) used three cameras to take images of aggregates moved in a conveyor belt system with constant speed of 8 cm/second. Aggregate volume was provided by combining the information in the three images of the particle areas. Particles were determined using a threshold value to distinguish between aggregate and background.

Kuo and Freeman (2000) construct three imaging shape indexes that characterized aggregates. Images were digitized into picture elements (pixels) with proper contrast. Aggregate dimensions, diameter and perimeter extracted from the differentiation of gray levels.

Fletcher et al. (2002 and 2003) built a system for measuring aggregate texture by using image processing technique. They analyzed a wide range of fine and coarse aggregates, quantifying textures, and angularities. Wavelet transform was used to map an image into a low-resolution image and a series of detail images. The average energy on the detail images was used as a texture parameter.

Gransberg et al. (2002 and 2005) used digital image processing in surface condition classifications. To quantify chip seal surface texture, the image was blurred to remove noise then filtered to detect edges from the local variation in the pixel gray intensity values. They computed the maximum value of the two-dimensional Fourier transform of a filtered image which was found correlated with a qualitative performance rating of the chip sealed surface pavement. The study showed that as a pavement surface deteriorates, the maximum Fourier transform value decreases.

A friction-coefficient prediction model was developed by Ergun et al. (2005) based on microtexture profiles measured by using an image analysis technique. The surface profile was recovered by scanning the surface using a razor blade illuminated from a light source. The shadow of the blade on the sample reveals the surface profile. The surface was recovered by accumulating surface profiles using series of images that captured by a camera with a magnification rate of 50.

Recently, Abbas et al. (2007) investigated the effectiveness of different mathematical methods in describing the three-dimensional surface textures of Portland cement concrete (PCC) pavements. X-ray computed tomography was used to scan the upper portion of core samples, resulting in a stack of two-dimensional grayscale images. The reconstructed three-dimensional surface topography was reduced to two-dimensional "map of heights" images, whereby the grayscale intensity of each pixel within the image represented the vertical location of the surface at that point with respect to the lowest point on the surface. The "map of heights" images were compared with the mean profile depth (MPD). A well correlation was obtained between the MPD and the PSD indexes with $R^2$ values ranging from 0.71 to 0.89.

The three-dimensional surface heights recovered by Ergun et al. or by Abbas et al. were generated from two dimensional profiles by accumulating series of measured two-dimensional profiles.

Surface to Image Models
Image Forming System

The surface of an object reflects a fraction of the incident illumination in a given direction on the basis of the optical properties of the surface material. The fraction of light reflected in a given direction is characterized by the surface orientation. In this case, the reflectance function $\phi(i,e,g)$ of the three angles; incident i, emergent e, and phase g, represents the reflectance characteristics of the surface (Woodham 1980 and Coleman and Jain 1982).

Figure 5:
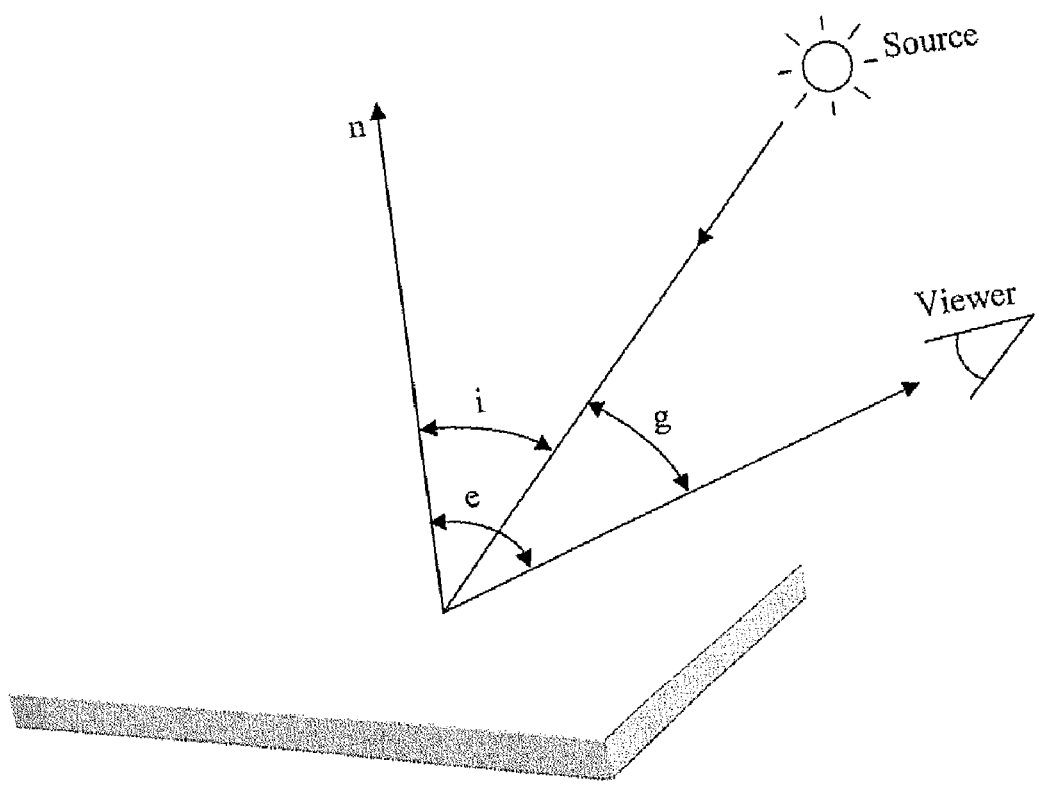
FIG. 5 is a perspective representation of the geometry of a general imaging system.

As shown in FIG. 5 the incident angle i and the emergent angle e are the inclination angles of the incident ray and emergent ray with respect to the surface normal, respectively. They are defined relative to local surface normal. The phase angle g is the angle between the incident and the emergent rays.

Figure 6:
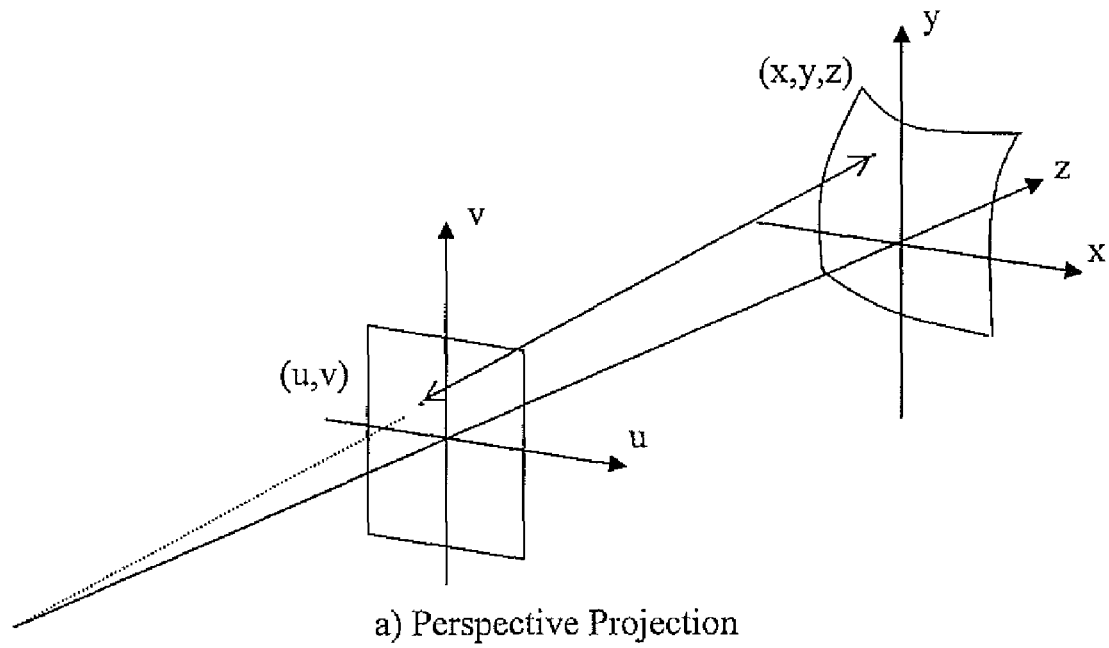
FIGS. 6a and 6b are schematic representations of the image projections.
Figure 6:
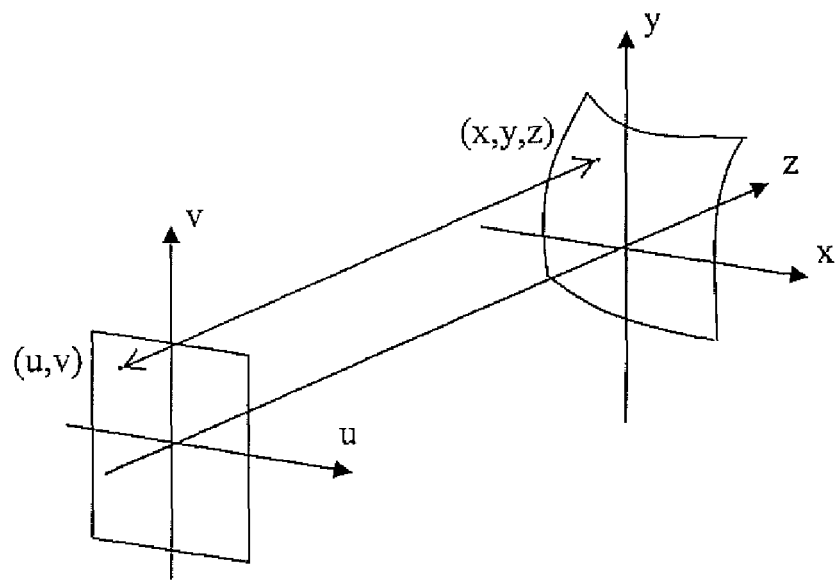

In general, image forming system is projected by either perspective transformation or orthographic transformation, as illustrated in FIG. 6. If the viewing distance is far away from the object relative to its size, the perspective projection is approximated as an orthographic projection.

Figure 7:
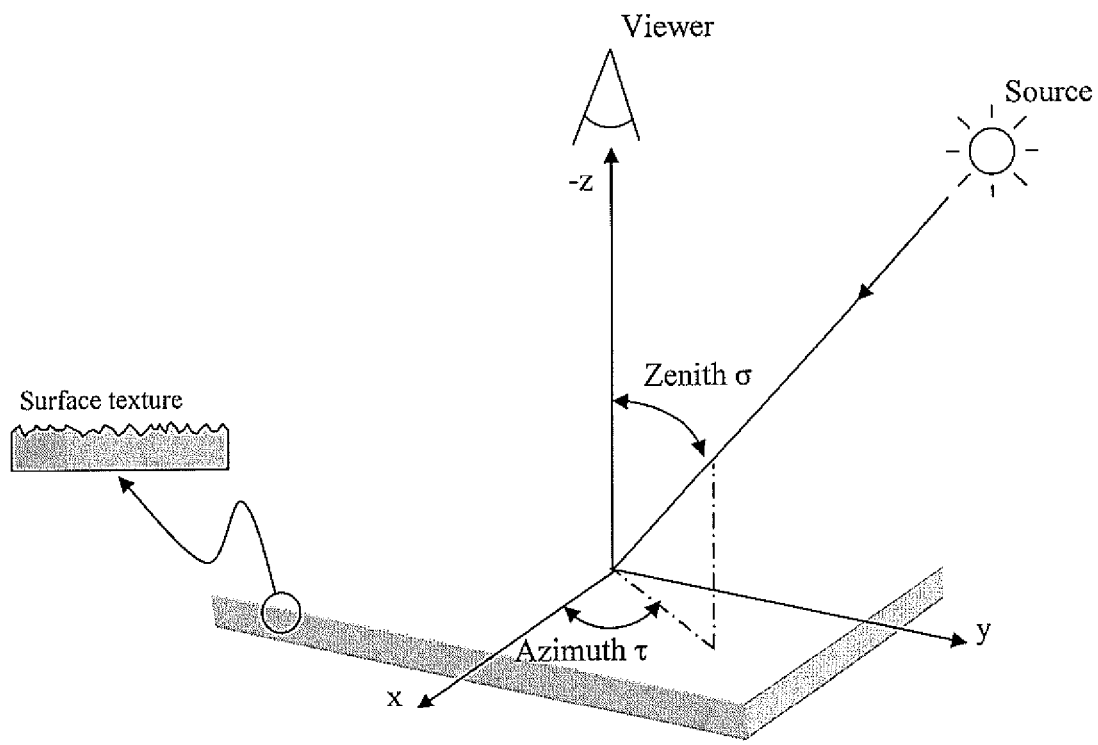
FIG. 7 is a schematic representation of the image forming system

The photometric stereo method assuming orthographic projection proposed by Woodham (1980) has been standardized by many researchers (e.g. Coleman and Jain 1982, McGunnigle 1998, and Gullón 2003). The coordinate system has been chosen such that the viewing direction is aligned with the negative z-axis (FIG. 7). Also, it is assumed that image coordinates (u,v) and object coordinates (x,y) could interchangeably refer to each other (e.g. u=x and v=y). Which means that object point (x,y,z) maps onto image point (u,v) as shown in FIG. 6b.

The same imaging system of Woodham is used in the present study where the viewer direction is aligned with the negative z-axis of the coordinate system. The surface of the sample is assumed globally flat and normal to the viewing direction. The system origin is at the centre of the sample surface. As the camera is far away from the sample surface relative to its size, orthographic projection is assumed. The light source is assumed to be a point source and is far away from the sample. Therefore, a constant incident illumination over the scene is assumed. The three angles i, e and g are replaced by the azimuth ($\tau$) and the zenith ($\sigma$) angles of the light source (FIG. 7). They are also called, respectively, illuminate tilt and slant angles.

If surface heights are defined by a function z(x,y) then, the surface orientation at each point (x,y) is expressed by the partial derivatives of the surface z as follows:

$$p(x, y) = \frac{\partial z(x, y)}{x} = z_x \quad (4.6)$$

$$q(x, y) = \frac{\partial z(x, y)}{y} = z_y \quad (4.7)$$

Thus, the surface normal at any point (x,y) is defined by the gradient quantities p and q.

The Reflectance Models

Figure 8:
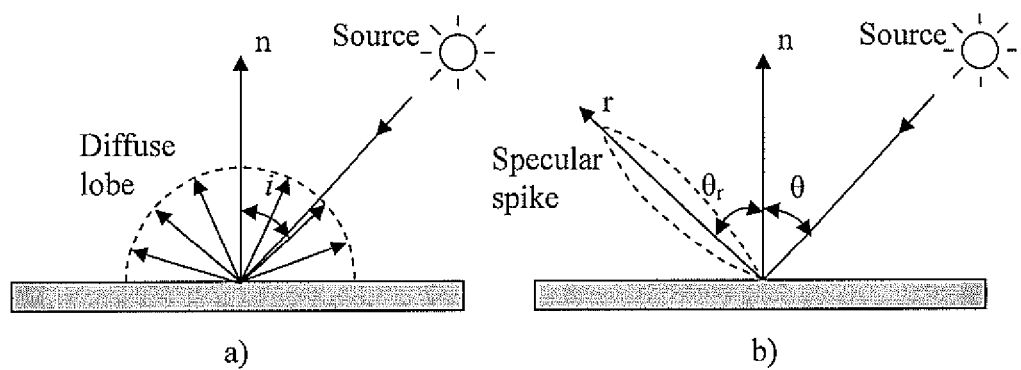
FIG. 8a is a schematic representation of diffuse reflection and FIG. 8b is a schematic representation of specular reflection.

Reflectance models describe how surface reflects lights according to its orientation and light direction. In the area of machine vision, the two main reflectance models are diffuse and specular models (Horn 1977). In diffuse (Lambertian) model, a surface reflects light equally in all direction. While in specular (non-Lambertian) model the surface reflects light in the reflectance direction only (FIG. 8). In fact, most of the surfaces are neither pure diffuse nor pure specular, therefore hybrid reflectance model which contains a specular components in addition to the diffuse component could be used.

Woodham (1980) used Lambertian model for determining surface orientation from three images. Coleman and Jain (1982) used Lambertian model with four-source photometric stereo to overcome specular distortion when obtaining shape of textured and specular surfaces.

Ikeuchi (1981) used specular model to determine the shape of specular surfaces by photometric stereo. Ikeuchi used a linear light source which is different from the illumination source used in this research.

Nayar et al. (1991) proposed a hybrid reflectance model as a unified reflectance framework to describe the reflection of light from smooth and rough surfaces.

In the following sections, the main reflectance models, diffuse, specular, and hybrid models, are discussed.

Lambertian Model

The Lambertian model is the most common reflectance model in machine vision (Horn 1977, Woodham 1980, Gullón 2003, and Zhang et al. 1999). The model is proposed in 1760 by Lambert who assumes that a diffuse surface reflects light uniformly in all direction. According to this assumption, a diffuse surface appears equally bright from all viewing directions. As illustrated FIG. 8a, for S a point light source at infinity, and when S illuminates straightly to the surface, the diffuse surface reflects the incoming light equally in all directions and independently of the illuminant direction.

The reflected intensity is proportional to the incident angle between the surface normal and the illuminant direction:

$$I = I_o \rho \cos(i) \qquad (4.8)$$

where:

I=the reflected intensity.

Io=the incident intensity.

ρ=the albedo; a reflectance factor that represents the proportion of light reflected with respect to the incident light.

The cosine of the incident angle, cos(i), is calculated using normalized dot products of the unit vector normal to the surface, $$n = \left[ \frac{-p}{\sqrt{p^2+q^2+1}}, \frac{-q}{\sqrt{p^2+q^2+1}}, \frac{1}{\sqrt{p^2+q^2+1}} \right],$$

and the unit vector, $S=[\cos(\tau)\sin(\sigma), \sin(\tau)\sin(\sigma), \cos(\sigma)]$, which points in the direction of light source. The corresponding reflectance map, R(p,q) that determines image intensity as a function of p and q, is given by:

$$R(p,q) = \rho \frac{-p\cos(\tau)\sin(\sigma) - q\sin(\tau)\sin(\sigma) + \cos(\sigma)}{\sqrt{p^2+q^2+1}} \qquad (4.9)$$

Equation (4.8) is rewritten in scalar form for each point (x,y):

$$i(x,y) = \qquad (4.10)$$
$$i_o \rho(x,y) \frac{-p(x,y)\cos(\tau)\sin(\sigma) - q(x,y)\sin(\tau)\sin(\sigma) + \cos(\sigma)}{\sqrt{p(x,y)^2 + q(x,y)^2 + 1}}$$

where:

i(x,y)=the reflected intensity at point (x,y).

$i_o$=the incident intensity at point (x,y). For a point light source at infinity, constant incident illumination over the scene is assumed; io=Io for all points.

Specular Model

FIG. 8b illustrates the concept of specular reflection (Zhang et al. 1999). If a point light source S illuminates to the surface, the specular surface reflects the light at the reflected direction r, where θ=θ_r. This means that specularity occurs when the incident angle of the light source is equal to the reflected angle. The specular reflection is described in simple form by the following delta function:

$$I_s = B\delta(\theta_s - 2\theta_r) \qquad (4.11)$$

where:

$I_s$=the specular brightness,

B=the strength of the specular component, $\theta_s$=the angle between the light source direction and the viewing direction, and $\theta_r$=the angle between the surface normal and the viewing direction.

Figure 9:
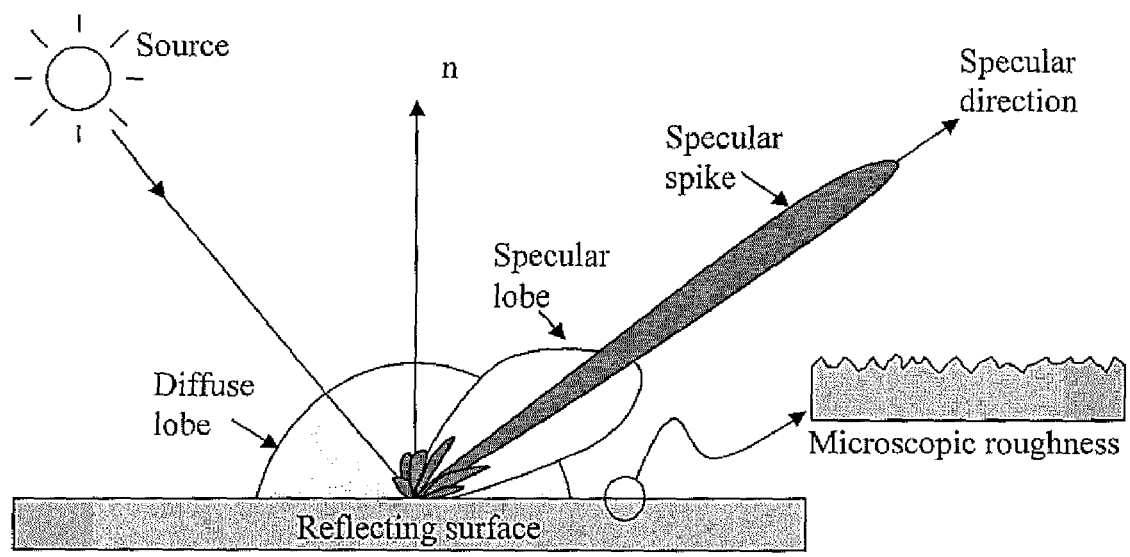
FIG. 9 is a schematic representation of reflection components for a hybrid reflectance model. (Nayar et al. 1991)

For smooth surface (perfect mirror), the light reaching the surface is reflected with the same angle forming a specular spike. The reflected intensity is zero in all directions except for a very narrow range around the direction of specular reflection. For rough surface, the specular spike spreads over a wide range of angles. In this case, the specular model defines by two main components; specular spike and specular lobe as shown in FIG. 9.

Hybrid Model

Nayar et al. (1991) proposed a hybrid reflectance model comprising three reflection components: the diffuse lobe, the specular lobe, and the specular spike as shown in FIG. 9. The diffuse lobe is distributed equally around the surface representing the internal scattering while the specular lobe represents the spread of single reflection according to surface roughness. The specular spike represents the perfect mirror reflection and it is the main reflectance for smooth surfaces.

The diffuse lobe and specular lobe components are mainly affected by surface roughness while specular spike is affected by surface smoothness. As the surface roughness increase, both diffuse lobe and specular lobe components are increased and specular spike is decreased. Nayar et al. concluded that, for a given wavelength of incident light, the specular spike and the lobe components, specular lobe and diffuse lobe, are comparable to one another only for a small range of roughness values.

Photometric Stereo Techniques

Introduction

Several techniques are available to recover three-dimensional shapes of objects (see Zhang et al. 1999). Of these techniques, the photometric stereo technique has been widely used in shape recovery. The recovered shape is expressed in surface gradient (p,q). Therefore a height recovery from surface gradient should be carried out using either local or global integration. In this chapter, the photometric stereo techniques followed by integration techniques are introduced in detail.

Classic Photometric Stereo Technique

The photometric stereo technique was proposed by Woodham (1980) and has been studied and extended by several researchers, such as Coleman and Jain (1982) and Lee and Kuo (1993). The idea of photometric stereo is to get three images under three different directions of incident illuminations, while the view direction is held constant. Assuming a constant light intensity, the reflected intensity, Equation (4.10), at any point (x,y) is a function of the three unknown, p, q, and p. Since image geometry is not changed, any three incident directions do not lie in a plane would provide sufficient information to determine p, q, and p at each point (x,y).

Let a set of images intensity values $i_1(x,y), i_2(x,y) \ldots$, and $i_n(x,y)$ which are obtained by varying the direction of incident illumination recorded at a point (x,y). Where $i_k(x,y)$ is image taken corresponding to a view at position k of incident illumination. Since imaging geometry is not changed, each picture element (x,y) in the set corresponds to the same object point and hence to the same photometric properties, p, q, and p. If the light intensity is constant then the effect of varying the direction of incident illumination is to change the reflectance map R (p,q). Suppose a set of three images and $\bar{I} = [i_1, i_2, i_3]^T$ is the column vector of intensity values recorded at a point (x,y) in each of the three view. If $\bar{s}_i = [s_{i1}, s_{i2}, s_{i3}]^T$ is a unit vector defining points in the direction of light source for the image i then the light source matrix [S] is $$[S] = \begin{bmatrix} s_{11} & s_{12} & s_{13} \\ s_{21} & s_{22} & s_{23} \\ s_{31} & s_{32} & s_{33} \end{bmatrix} \qquad (5.1)$$

Let $\overline{N}=[n_1,n_2,n_3]^T$ be the column vector corresponding to a unit surface normal at (x,y). Equation (4.8) is rewritten in matrix form for each point (x,y):

$$\overline{I}=\rho[S]\overline{N} \quad (5.2)$$

So that, $$\rho\overline{N}=[S]^{-1}\overline{I} \quad (5.3)$$

The inverse $[S]^{-1}$ exists only if the three vectors $\overline{s}_1$, $\overline{s}_2$ and $\overline{s}_3$ do not lie in a plane. In this case, the reflectance factor, $\rho(x,y)$, is computed by taking the magnitude of the right side of equation (5.3) because the surface normal, $\overline{N}$, is of unit length.

$$\rho=|[S]^{-1}\overline{I}| \quad (5.4)$$

After that the unit normal is computed as $$\overline{N}=(1/\rho)[S]^{-1}\overline{I} \quad (5.5)$$

Four-Source Photometric Stereo Technique

Coleman and Jain (1982) extended the photometric stereo technique of Woodham to a four-source photometric technique with the goal of overcoming specular distortion. Although three light sources are sufficient to recover a surface, the fourth source provides redundancy and is used to detect and correct the specular effects.

Figure 10:
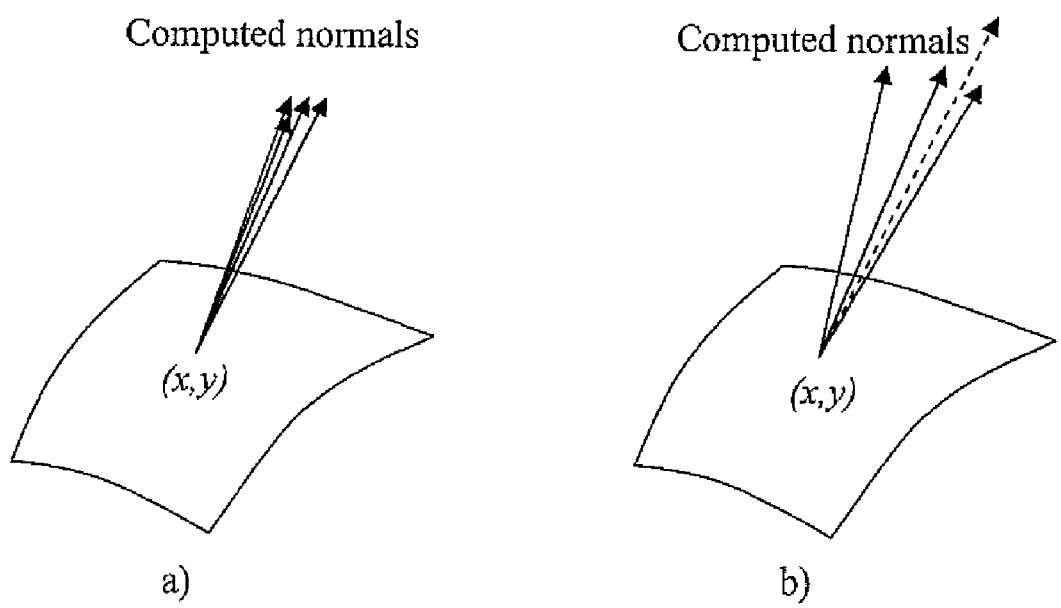
FIG. 10a is a schematic representation of computed normals for a specular component and FIG. 10b is a schematic representation of computed normals if specularity existed.

When a point on the surface is oriented such that its specular spike is in the same direction as one of the three light sources, a spike in reflected intensity is produced. In this case, the computed normal would be higher than the surface normal. A fourth source is add to detect the existence of specularity by computing four surface normal vectors, one normal for each combination of three images FIG. 10 illustrates the effect of specularity on the calculations of four surface normals; one from each three light source combination. At any given point (x,y) on the surface, if there is no specular component, the resulting four surface normals appears very close to each others as shown in FIG. 10a. In this case the surface normal is the average of the computed four surface normals.

If specularity exists in an image, its intensity value elevates the resulting surface normal causing a high deviation among the resulting four surface normals as shown in FIG. 10b. The existence of specularity causes a high deviation in both direction and magnitude of the vectors.

A thresholding procedure is used to eliminate specular effects. First, the relative deviation in the surface reflectance factor ρ at each point on the surface is computed using the formula:

$$\rho_{dev} = \left[\sum_{i=1}^{4}(\rho_i - \rho_{mean})\right] / (4\rho_{min}) \quad (5.6)$$

where:
$\rho_i$=the reflectance factor computed at (x,y) from each of the three source combinations.
$\rho_{mea}$=the average value of the computed reflectance factors at (x,y)
$\rho_{min}$=the minimum reflectance factor computed at (x,y)

Before computing the surface normal at each point (x,y), the relative deviation, $\rho_{dev}$ at each point is checked against a threshold value $\rho_t$ which is chosen to indicate a specular contribution. If $\rho_{dev}$ is greater than the largest amount of the reflectance deviation allowed, $\rho_t$, the surface normal is chosen from the combinations of the three intensity values which have the smallest reflectance factor. In the other hand, if there is no specular contribution ($\rho_{dev}$ is less than or equal to $\rho_t$), the normal surface is computed as the average of all four normals.

Simple Photometric Stereo Technique

McGunnigle (1998) used a simple photometric stereo algorithm that avoids inverse matrix calculations by placing the lights with the same zenith angle and azimuth angles in 90° increment. Consider an illuminated surface, whose intensity corresponds to Equation (4.10). If the surface is illuminated from τ=0°, 90° or 180°, Equation (4.10) is simplified to the following three equations respectively:

$$i_0(x,y) = i_o\rho(x,y)\frac{-p(x,y)\sin(\sigma) + \cos(\sigma)}{\sqrt{p(x,y)^2 + q(x,y)^2 + 1}} \quad (5.7)$$

$$i_{90}(x,y) = i_o\rho(x,y)\frac{-q(x,y)\sin(\sigma) + \cos(\sigma)}{\sqrt{p(x,y)^2 + q(x,y)^2 + 1}} \quad (5.8)$$

$$i_{180}(x,y) = i_o\rho(x,y)\frac{p(x,y)\sin(\sigma) + \cos(\sigma)}{\sqrt{p(x,y)^2 + q(x,y)^2 + 1}} \quad (5.9)$$

where $i_0(x,y)$, $i_{90}(x,y)$, and $i_{180}(x,y)$ are image intensities at point (x,y) when surface illuminated from τ=0°, 90° and 180° respectively.

Adding $i_0(x,y)$ and $i_{180}(x,y)$ produces:

$$i_{NL}(x,y) = i_0(x,y) + i_{180}(x,y) = \frac{2i_o\rho(x,y)\cos(\sigma)}{\sqrt{p(x,y)^2 + q(x,y)^2 + 1}} \quad (5.10)$$

Dividing Equations (5.7) and (5.8) by (5.10) results in two linear equations which are independent of albedo, $\rho(x,y)$, and incident intensity, $i_o$ $$i_p(x,y) = \frac{i_0(x,y)}{i_0(x,y) + i_{180}(x,y)} = \frac{-p(x,y)\tan(\sigma) + 1}{2} \quad (5.11)$$

$$i_q(x,y) = \frac{i_{90}(x,y)}{i_0(x,y) + i_{180}(x,y)} = \frac{-q(x,y)\tan(\sigma) + 1}{2} \quad (5.12)$$

and the surface gradient may be computed as $$p(x,y) = \frac{1 - 2i_p(x,y)}{\tan(\sigma)} \quad (5.13)$$

$$q(x,y) = \frac{1 - 2i_q(x,y)}{\tan(\sigma)} \quad (5.14)$$

This simple and fast technique requires capturing three images at tilt angles of 90° increments and applying equations (5.13) and (5.14) to compute gradient of Lambertian surface.

Optimal Light Source Position

The illumination position affects the accuracy of shape recovery. Therefore, selecting the optimal light source position has been extensively studied for a variety of types of sources (Lee and Kuo, 1993, Gullón 2003, Drbohlav and Chantler 2005, and Spence and Chantler 2006).

In their proposed two-image photometric stereo algorithm, Lee and Kuo (1993) examined the optimal illumination condition that led to the best shape recovery. they found that the optimal lighting condition is more sensitive to the difference in tilt angles than the slant angles as long as they are between range 30° and 60°. The optimal lighting condition is achieved when the gradient direction of the reflectance map for an image corresponded to the tangential directions of the reflectance map of the other image producing a difference of 90° between the illumination tilt angles.

Gullón (2003) investigated the optimal position for different two-image photometric stereo techniques. The same conclusion was achieved and the optimal lighting conditions for two lights are Zenith angles within the range $30° \leq \sigma < 60°$ Azimuth angles with 90° increment.

Spence and Chantler (2006) studied optimal illumination for three-image photometric stereo using sensitivity analysis. They found that an orthogonal configuration is optimal with constant slant angle. The optimal tilt angles are separated by 120° while the optimal slant angle is 90° for smooth surface textures and 55° for rough surface textures.

For three lights, Drbohlav and Chantler (2005) studied the optimal light configurations of photometric stereo lighting in the presence of camera noise. For three lights, any triplet of orthogonal light directions would be optimum. Assuming that the camera noise is additive and normally distributed with zero mean and variance VAR, the optimal (minimum) uncertainty in the scaled normal is 9 VAR/n. For case of more than three lights, an optimal configuration is achieved when light sources are equally separated on a circle of uniform slant. The optimal slant is independent of n and is equal to 54.74°.

Depth Recovery from Surface Gradient

Recovering depth $z(x,y)$ from surface gradient $p(x,y)$ and $q(x,y)$ may be performed by using either local integration techniques or global integration techniques.

Local path integration techniques are easy to implement and computationally efficient; however, the use of multiple paths is necessary to minimize the propagation of errors. In global techniques, surface integration is treated as an optimization problem.

Local Integration

Coleman and Jain (1982) converted surface normals to depth heights by approximating the curve between any two adjacent points by its average tangent line assuming that the points are very close relative to the surface size. The algorithm is used to propagate depth values after choosing an arbitrary depth $z(x,y)$ value for the point in the center of the image.

Healey and Jain (1984) presented an improved method for depth recovery considering the eight points surrounding a given point. The system of nine constraint equations specified by nine points is solved by knowing the depth of one of these points. Although the improved method is more accurate than the two-point method, it is not applied to border points.

Wu and Li (1988) used multiple path-independent line integrals to recover depth. First, an arbitrary depth value is assumed for any point $(x_0,y_0)$ in the image, then the relative depth at every point $z(x,y)$ is determined by computing line integrals taking multiple paths to reduce the error by averaging.

Wu and Li stated that the integral of p and q along closed curve is equal to zero. Thus, recovered depth is obtained from the path-independent integral of p and q as follows:

$$z(x,y) = z(x_0, y_0) + \int_\gamma p(x,y)dx + q(x,y)dy \quad (5.15)$$

where $\gamma$ is an arbitrary specified integration path from $(x_0,y_0)$ to $(x,y)$. To reduce error, the relative height is found by averaging values calculated using different integration paths.

Figure 11:
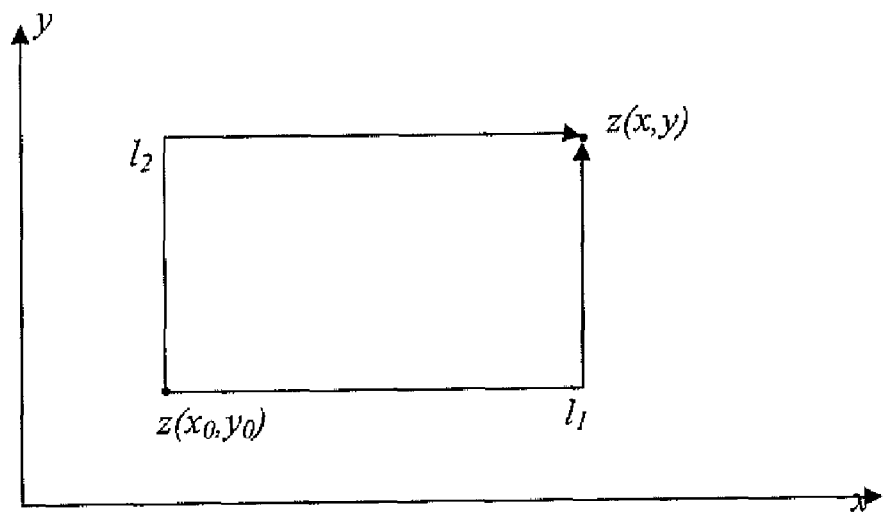
FIG. 11 is a schematic representation of two integration paths between $(x_0,y_0)$ and x,y).

If two paths are chosen as shown in FIG. 11, the depth $z(x,y)$ at any point $(x,y)$ becomes:

$$\begin{aligned} z(x,y) &= z(x_0, y_0) + \frac{1}{2}\int_{L_1}(pdx+qdy) + \frac{1}{2}\int_{L_2}(pdx+qdy) \\ &= z(x_0, y_0) + \frac{1}{2}\left(\int_{y_0}^{y} q(x_0,y)dy + \int_{x_0}^{x} p(x,y)dx\right) + \\ &\quad \frac{1}{2}\left(\int_{x_0}^{x} p(x,y_0)dx + \int_{y_0}^{y} q(x,y)dy\right) \end{aligned} \quad (5.16)$$

For discrete integration procedures, using a trapezoidal formula and choosing point at $(i_0,j_0)$ as a reference point, the relative depth at any point $(i,j)$ is calculated as:

$$\begin{aligned} z(i,j) &= z(i_0,j_0) + \frac{1}{2}\left(\frac{q(i_0,j_0)+q(i_0,j)}{2} + \sum_{k=j_0+1}^{j-1} q(i_0,k)\right)\Delta y + \\ &\quad \frac{1}{2}\left(\frac{p(i_0,j)+p(i,j)}{2} + \sum_{k=i_0+1}^{i-1} p(k,j)\right)\Delta x + \\ &\quad \frac{1}{2}\left(\frac{p(i_0,j_0)+p(i,j_0)}{2} + \sum_{k=i_0+1}^{i-1} p(k,j_0)\right)\Delta x + \\ &\quad \frac{1}{2}\left(\frac{q(i,j_0)+q(i,j)}{2} + \sum_{k=j_0+1}^{j-1} q(i,k)\right)\Delta y \end{aligned} \quad (5.17)$$

where $\Delta x$ and $\Delta y$, the sampling intervals in x-direction and y-direction, respectively, are usually assumed 1 pixel.

Global Integration

Global integration techniques (Horn and Brooks 1986, Frankot and Chellappa 1988, Horn 1990, and Wei and Klette 2002) are based on solving the nonlinear partial differential equation in x and y under the following consistency constrain $$\frac{\partial}{\partial y}z_x = \frac{\partial}{\partial x}z_y \quad (5.18)$$

This constrain is achieved by selecting the surface slope estimate which minimize the following function:

$$w = \int\int [|z_x - p|^2 + |z_y - q|^2]dxdy \quad (5.19)$$

Frankot and Chellappa simplify the minimization problem by representing the surface slopes as a finite set of integrable basis functions, each satisfying Equation (5.18). Because of the orthogonality of the Fourier basis functions, Fourier transform of the surface function provides a simplified and computationally efficient solution.

Considering that the Fourier transformer of the surfaces function z(x,y) is $$Z(u, v) = \int_{-\infty}^{+\infty} \int_{-\infty}^{+\infty} z(x, y) \cdot e^{-j(u \cdot x + v \cdot y)} dx dy \quad (5.20)$$

and the inverse Fourier transform is $$z(x, y) = \frac{1}{2\pi} \int_{-\infty}^{+\infty} \int_{-\infty}^{+\infty} Z(u, v) \cdot e^{-j(u \cdot x + v \cdot y)} du dv \quad (5.21)$$

where
j=the imaginary unit.
u, v=The spatial frequencies in the x and y direction, respectively.
According to the differentiation properties of the Fourier transform and using the identities $$P(u,v) \leftrightarrow juZ(u,v) \quad (5.22)$$

$$Q(u,v) \leftrightarrow jvZ(u,v) \quad (5.23)$$

Then the surface height spectrum is obtained from $$Z(u, v) = \frac{-juP(u, v) - jvQ(u, v)}{u^2 + v^2} \quad (5.24)$$

In order to improve the accuracy and to strength the relation between the estimated surface and the original image, Wei and Klette (2002) extended the minimization function of Equation (5-19) to $$w = \int \int [|z_x - p|^2 + |z_y - q|^2] dx dy + \quad (5.25)$$
$$\lambda \int \int [|z_x|^2 + |z_y|^2] dx dy + \mu \int \int [|z_{xx}|^2 + 2|z_{xy}|^2 + |z_{yy}|^2] dx dy$$

where the subscripts indicate partial derivatives. λ and µ are nonnegative parameters used to adjust the weighting between constraints. The second term of the right-hand is a small deflection approximation of the surface area, and the third term is a small deflection approximation of the surface curvature.

Minimizing Equation (5.25) by using Fourier transformation result in surface height spectrum $$Z(u, v) = \frac{-juP(u, v) - jvQ(u, v)}{(1 + \lambda)(u^2 + v^2) + \mu(u^2 + v^2)^2} \quad (5.26)$$

Both equations (5.24) and (5.26) are not defined at the point (u,v)=(0,0): The average mean level of the surface should be assumed.

The minimization algorithm is implemented as a part of an iterative process where integrability is enforced at the cost of oversmoothing the surface estimate. For height recovery of rough surfaces, Gullón (2003) implemented this technique in a noniterative manner, so that the surface is not oversmoothed. In the rest of this study, when global integration technique is used the surface heights are recovered from surface orientations by applying the noniterative algorithm.

Proposed Photometric Stereo System
Introduction

Although photometric stereo techniques have been successfully used to recover surface texture (McGunnigle 1998 and Gullón 2003), applying such techniques to recover pavement surface is complicated because of the following conditions:

The dark monotone of the pavement surface requires high illumination intensity to produce a reasonable variation in surface reflectance;

Since stereo techniques are based on surface reflectance variation (shadow), the system should be able to distinguish between changes in gray levels from light reflectance and those from material color;

The system should be isolated from the ambient environment to reduce image noise;

Pavement surface materials may cause some specularity or shadow effects. These effects should be detected and eliminated; and The direction and type of lighting affect system accuracy; therefore, different illumination angles should be tested.

Figure 12:
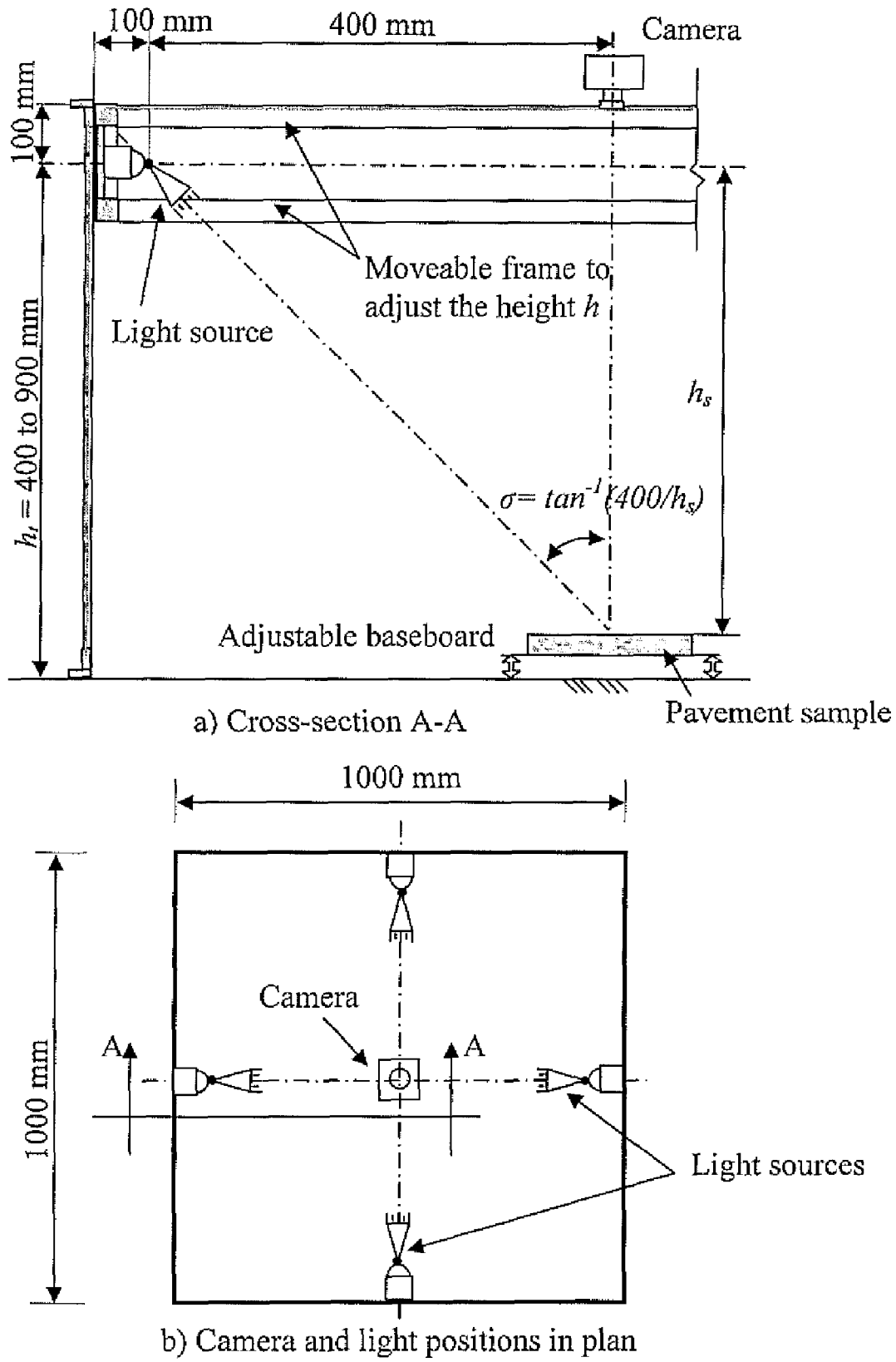
FIG. 12a is a cross section view and FIG. 12b is a plan view of a four-source photometric stereo system.

FIG. 12 shows the proposed four-source photometric stereo system. A digital still camera and four light sources are mounted in a retractable frame to allow height and angle adjustment of the light sources. Each light source is mounted at a center of one of the frame sides so that the sample is illuminated from four azimuth angles: τ=0°, 90°, 180° and 270°. The entire system is enclosed in a covered box that isolates the sample from ambient light.

Digital Camera Specifications

A 5.1 effective megapixel digital still camera with a 12× optical zoom lens is used. By using the 12× optical zoom lens and the macro function, the camera is capable of capturing images of close objects.

Exposure and focus are controlled manually by overriding the automated features of the camera. For a particular sample, the settings are fixed for each set of photos.

Lighting System

A 50 W halogen narrow angle source is used to provide high illumination intensity. Because of the narrow angle of the source (10°), it is assumed that the source produces constant incident illumination over the scene with parallel lighting direction.

Figure 13:
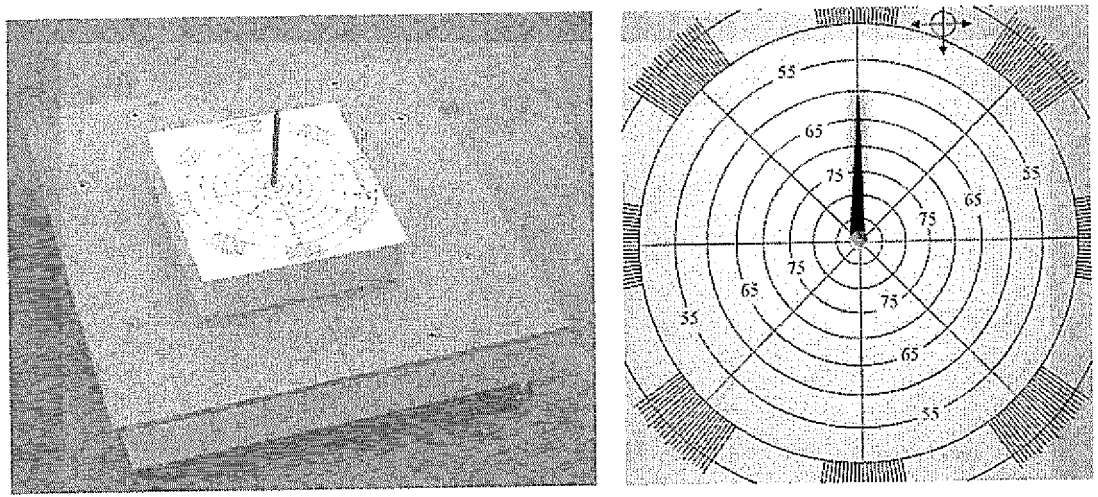
FIG. 13a is an illustration of a baseboard template used to adjust the height of the template.
FIG. 13b is an illustration of the calibration of light direction using shadow of a nail.

The lighting source elevation (frame elevation) above the sample surface is adjustable in the range of 400 to 900 mm, with 50 mm increments. Given the locations of the light sources and the sample, zenith angles (σ) can be varied from 25 to 55°. At any height of the lighting source, $h_s$(mm), the zenith angle is computed as $\sigma=\tan^{-1}(400/h_s)$. The light source height and inclination are adjusted so that the light direction matches the specified zenith angle. An angle alignment board is used to verify vertical and horizontal illumination directions (FIG. 13a). A nail mounted into the center of a block protrudes 58 mm vertically from the top surface. On the basis of the length of the nail, a template is used to calibrate the direction of the illumination from the shadow of the nail. An adjustable baseboard is used to keep the surface heights for both the sample and the alignment board at the same level (FIG. 13b).

The four light sources should also be calibrated to produce the same illumination intensity. This outcome is achieved by taking four photos, one from each light source, of a uniform and smooth white sheet of paper to compute an adjustment coefficient matrix. Adjustment coefficients for each pixel under each of the four lighting sources are used to calibrate subsequent images taken under each of the four sources.

Optimal Lighting Position

As discussed in section 5.5, in the case of more than three sources, one of the optimal configurations is achieved when light sources are equally spaced on a circle of uniform azimuth angles. Therefore in the proposed system, locating azimuth angles with a 90° increment is one of the optimal configurations.

Previous studies found that the optimal zenith angle ($\sigma$) depends on texture depth and is expected in the neighbourhood of 30° for rough surfaces.

Pavement Surface Texture Recovery System

Figure 14:
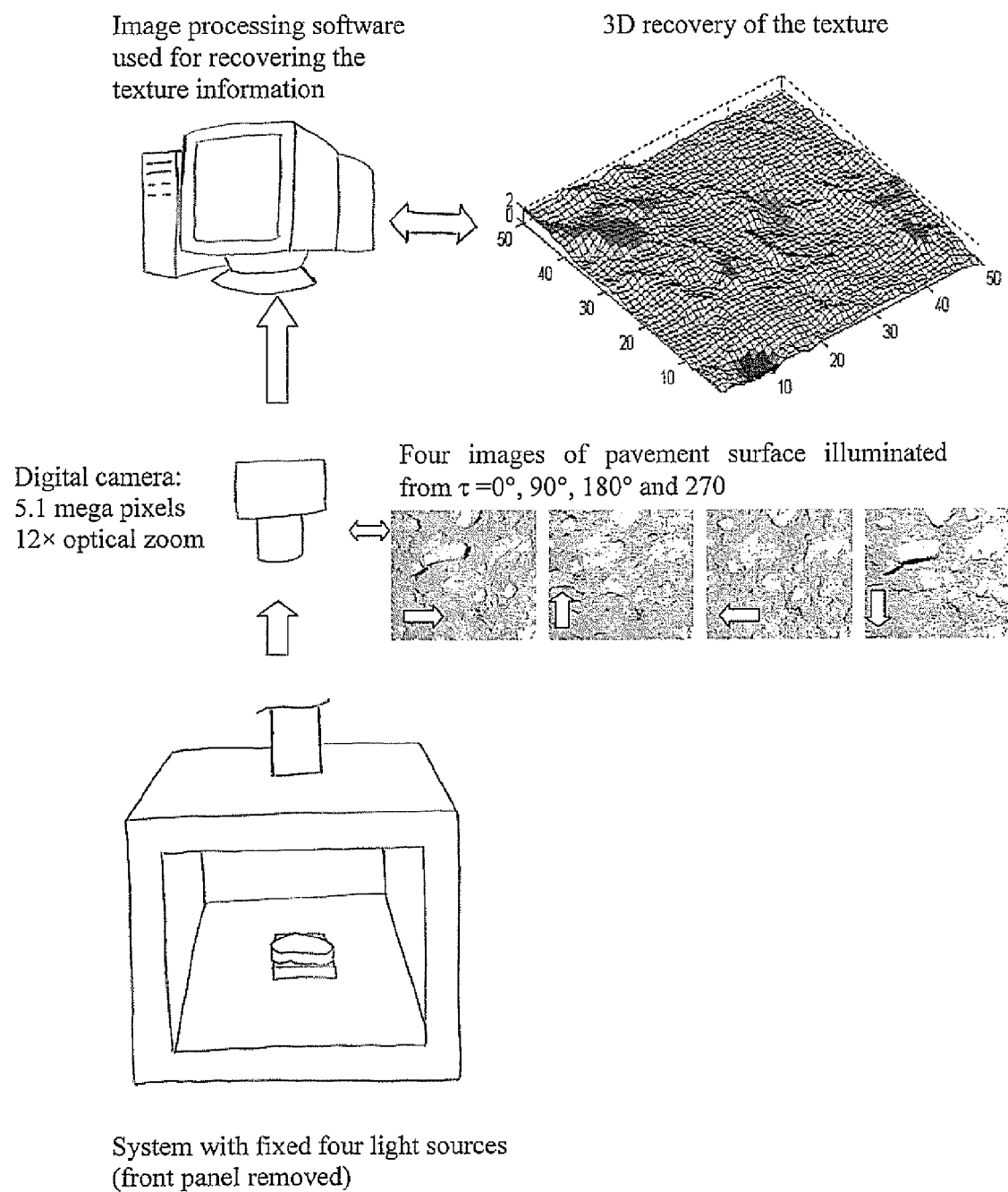
FIG. 14 is a schematic representation of the method of pavement surface texture recovery.

FIG. 14 summarizes the proposed surface recovery technique. The digital camera captures all images under manual exposure mode, in which illumination, zoom, focus, shutter speed, aperture, and exposure are set to fixed values so that the changes in image intensities are independent of the camera settings. The scene is isolated from ambient lights; therefore, the changes in pixel intensities are caused only by surface orientation and reflectance properties. The apparatus must be positioned on the pavement surface for the duration required to capture four images of the surface illuminated from four angles.

An image-processing algorithm for computing surface orientations from image intensities has been developed. The surface heights are recovered by using global integration to integrate surface orientation. The algorithm also computes such surface texture indicators as mean profile depth and root mean square roughness.

Removing Shadow and Specular Effects

Introduction

Although three light sources are sufficient to recover a surface, the fourth source provides redundancy and is used to detect and remove shadow or specularity effects if any of them existed.

In this chapter, a new four-source photometric stereo technique[1] is introduced. The proposed technique can detect and eliminate the specularity effect using image intensity. There is no need for computing four surface normals to determine the relative deviation in the surface reflectance and hence detect the specular effect.

[1] The proposed techniques has been published in the Graphics, Vision, and Image Processing journal (El Gendy and Shalaby 2007A)

Since four light sources are used in this study, McGunnigle (1998) simple three-source photometric stereo algorithm is extended to four sources. Consider an illuminated surface, whose intensity corresponds to Equation (4.5). If the surface is illuminated from $\tau=0°$, 90°, 180°, and 270°, Equation (4.5) is simplified to the following four equations respectively:

$$i_0(x, y) = i_o\rho(x, y)\frac{-p(x, y)\sin(\sigma) + \cos(\sigma)}{\sqrt{p(x, y)^2 + q(x, y)^2 + 1}} \quad (7.1)$$

$$i_{90}(x, y) = i_o\rho(x, y)\frac{-q(x, y)\sin(\sigma) + \cos(\sigma)}{\sqrt{p(x, y)^2 + q(x, y)^2 + 1}} \quad (7.2)$$

$$i_{180}(x, y) = i_o\rho(x, y)\frac{p(x, y)\sin(\sigma) + \cos(\sigma)}{\sqrt{p(x, y)^2 + q(x, y)^2 + 1}} \quad (7.3)$$

$$i_{270}(x, y) = i_o\rho(x, y)\frac{q(x, y)\sin(\sigma) + \cos(\sigma)}{\sqrt{p(x, y)^2 + q(x, y)^2 + 1}} \quad (7.4)$$

where $i_0(x,y)$, $i_{90}(x,y)$, $i_{180}(x,y)$ and $i_{270}(x,y)$ are image intensities at point (x,y) when surface illuminated from $\tau=0°$, 90°, 180° and 270° respectively.

Using Equations (7.1) to (7.4), and since any three images would provide sufficient information to determine p, q, and $\rho$ at each point (x,y), each image is estimated using the rest of the other three images as follows:

$$\hat{i}_0(x,y)=-i_{180}(x,y)+i_{90}(x,y)+i_{270}(x,y) \quad (7.5)$$

$$\hat{i}_{90}(x,y)=-i_{270}(x,y)+i_0(x,y)+i_{180}(x,y) \quad (7.6)$$

$$\hat{i}_{180}(x,y)=-i_0(x,y)+i_{90}(x,y)+i_{270}(x,y) \quad (7.7)$$

$$\hat{i}_{270}(x,y)=-i_{90}(x,y)+i_0(x,y)+i_{180}(x,y) \quad (7.8)$$

where $\hat{i}_0(x,y)$, $\hat{i}_{90}(x,y)$, $\hat{i}_{180}(x,y)$ and $\hat{i}_{270}(x,y)$ are the estimated image intensities of $i_0(x,y)$, $i_{90}(x,y)$, $i_{180}(x,y)$ and $i_{270}(x,y)$ respectively.

If specular component does not exist, the difference between any original and estimated image, $i(x,y)-\hat{i}(x,y)$, is almost zero or very small value assuming that the noise is normally distributed with zero mean. Otherwise the specular component increases the original image intensity; e.g. $i(x,y)-\hat{i}(x,y)>0$. To overcome the present of specular, the difference between original and estimated value is examined against a predetermine threshold, $i_{thr}$. Using Equations (7.5) to (7.8), these differences is rewritten as:

$$i_0(x,y)-\hat{i}_0(x,y)=(i_0(x,y)+i_{180}(x,y))-(i_{90}(x,y)+i_{270}(x,y)) \quad (7.9)$$

$$i_{90}(x,y)-\hat{i}_{90}(x,y)=(i_{90}(x,y)+i_{2780}(x,y))-(i_0(x,y)+i_{180}(x,y)) \quad (7.10)$$

$$i_{180}(x,y)-\hat{i}_{180}(x,y)=(i_0(x,y)+i_{180}(x,y))-(i_{90}(x,y)+i_{270}(x,y)) \quad (7.11)$$

$$i_{270}(x,y)-\hat{i}_{270}(x,y)=(i_{90}(x,y)+i_{270}(x,y))-(i_0(x,y)+i_{180}(x,y)) \quad (7.12)$$

Equations (7.9) to (7.12) is summarized in one rule

```
If (i₀(x,y) + i₁₈₀(x, y)) > (i₉₀(x,y) + i₂₇₀(x,y) +]i_thr then
    Specular component exists in either i₀(x,y) or i₁₈₀(x,y)
Else if (i₉₀(x,y) + i₂₇₀(x,y)) > (i₀(x,y) + i₁₈₀(x,y)) + i_thr then
    Specular component exists in either i₉₀(x,y) or i₂₇₀(x,y)
Else
    No specular component exists
End if
```

Non-Specular Surface

When no specular component exists, the surface gradient is calculated directly from the four images. Adding the four images, Equation (5.10) is rewritten as follows:

$$i_{NL}(x, y) = i_0(x, y) + i_{90}(x, y) + i_{180}(x, y) + i_{270}(x, y) = \frac{4i_o\rho(x, y)\cos(\sigma)}{\sqrt{p(x, y)^2 + q(x, y)^2 + 1}} \quad (7.13)$$

and Equations (511) and (5.12) are $$i_p(x, y) = \frac{i_0(x, y) - i_{180}(x, y)}{i_{NL}(x, y)} = \frac{-p(x, y)\tan(\sigma) + 1}{2} \quad (7.14)$$

-continued $$i_q(x, y) = \frac{i_{90}(x, y) - i_{270}(x, y)}{i_{NL}(x, y)} = \frac{-q(x, y)\tan(\sigma) + 1}{2} \quad (7.15)$$

then the surface gradient may be computed from Equations (5.13) and (5.14).

Specular Surface

Image intensity that has specularity contribution should be excluded from the calculation of the surface gradients. Detecting specular component that may exist in either $i_{90}(x,y)$ or $i_{270}(x,y)$ is described in detail then similar conclusion is applied to detect specularity in $i_0(x,y)$ or $i_{180}(x,y)$.

If specular component exists in $i_{90}(x,y)$ or $i_{270}(x,y)$, $p(x,y)$ is computed from Equation (5.13) which is independent of $i_{90}(x,y)$ and $i_{270}(x,y)$. Then, the problem is limited to which image which image, $i_{90}(x,y)$ or $i_{270}(x,y)$, is used to compute $q(x,y)$. As shown by Coleman and Jain (1982), specular component raises the magnitude of surface normal. Since $p(x,y)$ is computed independently of specular component, the raise in surface normal magnitude is from $q(x,y)$ only. Therefore, image intensity that provides the largest value of $q(x,y)^2$ is excluded.

Equation (5.14) can be expanded to include either $i_{90}(x,y)$ or $i_{270}(x,y)$ as follows:

$$q(x, y) = \frac{i_{NL}(x, y) - 2i_{90}(x, y)}{i_{NL}(x, y)\tan(\sigma)} \text{ or } \frac{i_{NL}(x, y) - 2i_{270}(x, y)}{i_{NL}(x, y)\tan(\sigma)} \quad (7.16)$$

The higher $(i_{NL}(x,y)-2i_\theta(x,y))^2$, the higher the corresponding $q(x,y)^2$, where $i_\theta(x,y)$ is intensity at $(x,y)$ for the image illuminated form the angle $\theta$; e.g $\theta=90°$ or $270°$.

Figure 15:
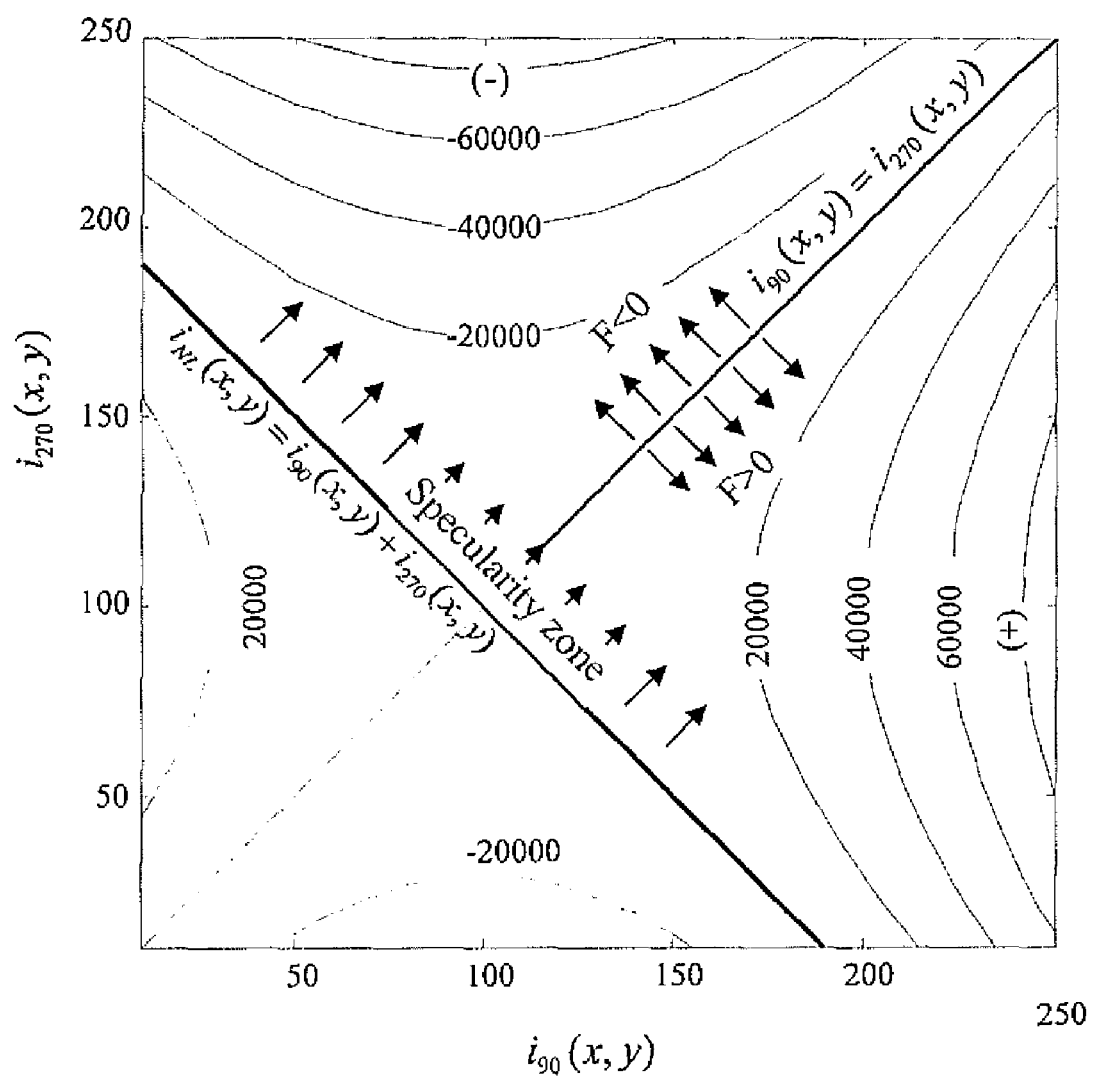
FIG. 15 is a schematic representation of a specular indictor for $i_{NL}(x,y)=180$.

Let F, an indicator used to determine image that has specular component as follows:

$$F=(i_{NL}(x,y)-2i_{90}(x,y))^2-(i_{NL}(x,y)-2i_{270}(x,y))^2 \quad (7.17)$$

Where F>0 indicates that specular component exit in $i_{90}(x,y)$ and F<0 indicates that specular component exists in $i_{270}(x,y)$. FIG. 15 shows contour lines for F at $i_{NL}(x,y)=180$. In the specular zone, $i_{90}(x,y)+i_{270}(x,y)>i_{NL}(x,y)$, The line $i_{90}(x,y)=i_{270}(x,y)$ separates between the two conditions F>0 and F<0 which means the specular component exists in the image that has the highest intensity. This conclusion would make the algorithm simple and fast by directly comparing image intensities before start computing surface normals. Although pixel under specular condition looks shinier than without specularity component, its intensity still lower than the corresponding intensity in the reverse direction.

Figure 16:
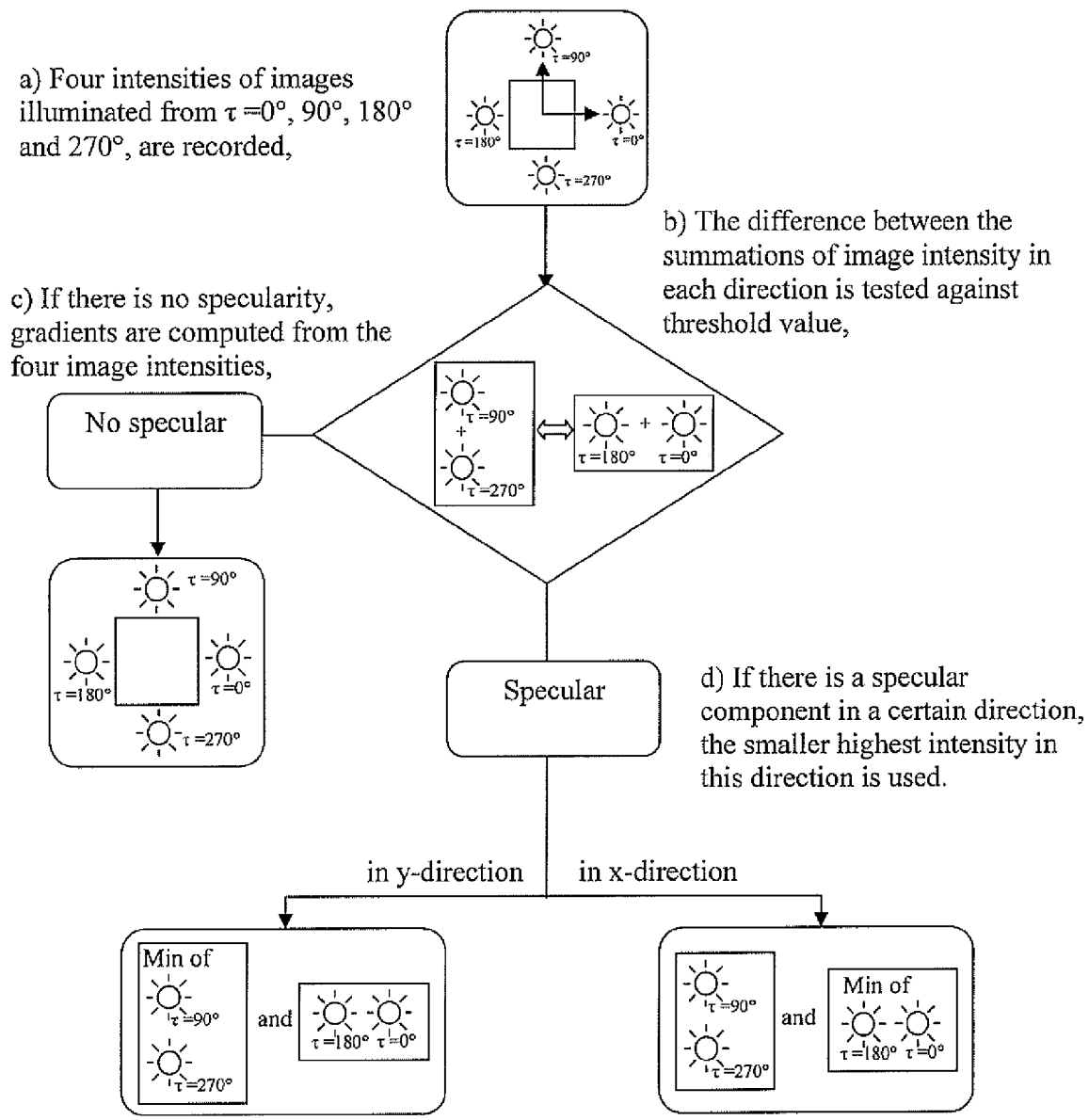
FIG. 16 is a schematic representation of the specular surface recovery method.

The proposed recovery technique is summarized in the flowchart of FIG. 16. If the specularity exists in a certain direction, the largest intensity value in this direction will be excluded and $i_{NL}(x,y)$ is computed from intensities in the other direction. The algorithm is simple to implement. The intensity values are directly used to detect the existence of specularity. There is no need to calculate the four reflectance factors or the four surface normals.

Experimental Work

Figure 17:
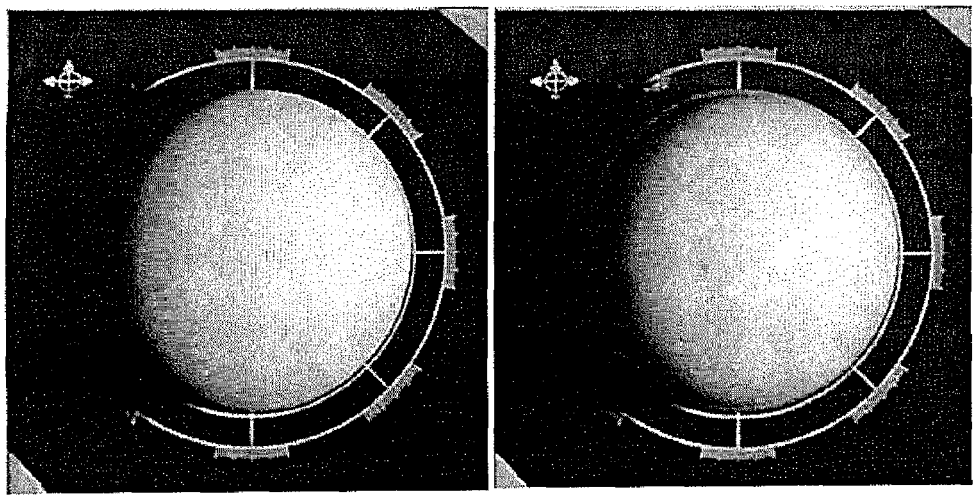
FIGS. 17a and 17b are illustrations of a spherical surface 6 cm in diameter and illuminated at tilt angle of 0, for a diffuse surface and for a specular surface respectively.

An image of a spherical diffuse surface is captured to validate the model. The surface is 6 cm in diameter and illuminated at tilt angle of 0°. A set of four images would be equivalent to the rotation of the image with angles of 90° increments. Another image is taken after covering the sphere with a thin transparent plastic film to give the surface a specular contribution (FIG. 17).

Optimal Light Source Position

As optimal illumination angle is required, also specular contribution should appear in only one image. Further more, illuminating sphere at slant angle results in a shade in part of the sphere surface. Since shadow is not considered, only the area of the semisphere that does not have shadow in any of the images is tested. For this example, $\sigma=33°$ is an appropriate illumination angle that gives specular contribution in only one image at a time within the area that has no shadow in any of the images.

Results

Figure 18:
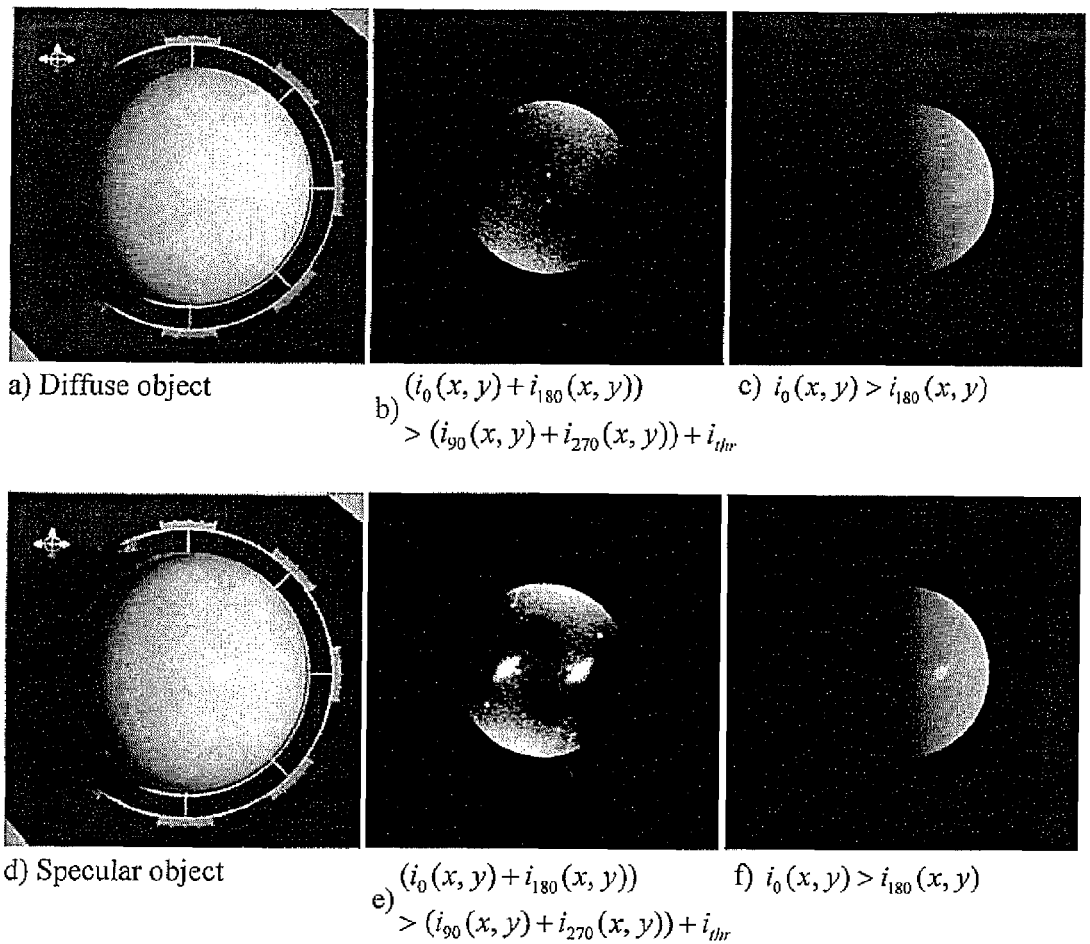
FIGS. 18a and 18b are schematic representations of the steps for detecting specularity for a diffuse object and for a specular object respectively.

FIG. 18 shows the intensity comparisons for the two surfaces. The specularity threshold is selected based on the average intensity over the entire scene. The maximum difference between $(i_0(x,y)+i_{180}(x,y))$ and $(i_{90}(x,y)+i_{270}(x,y))$ is 16% and 66% of the image average intensity for diffuse and specular surfaces, respectively. Two threshold values are examined: 20% and 30% of the image average intensity.

Figure 19:
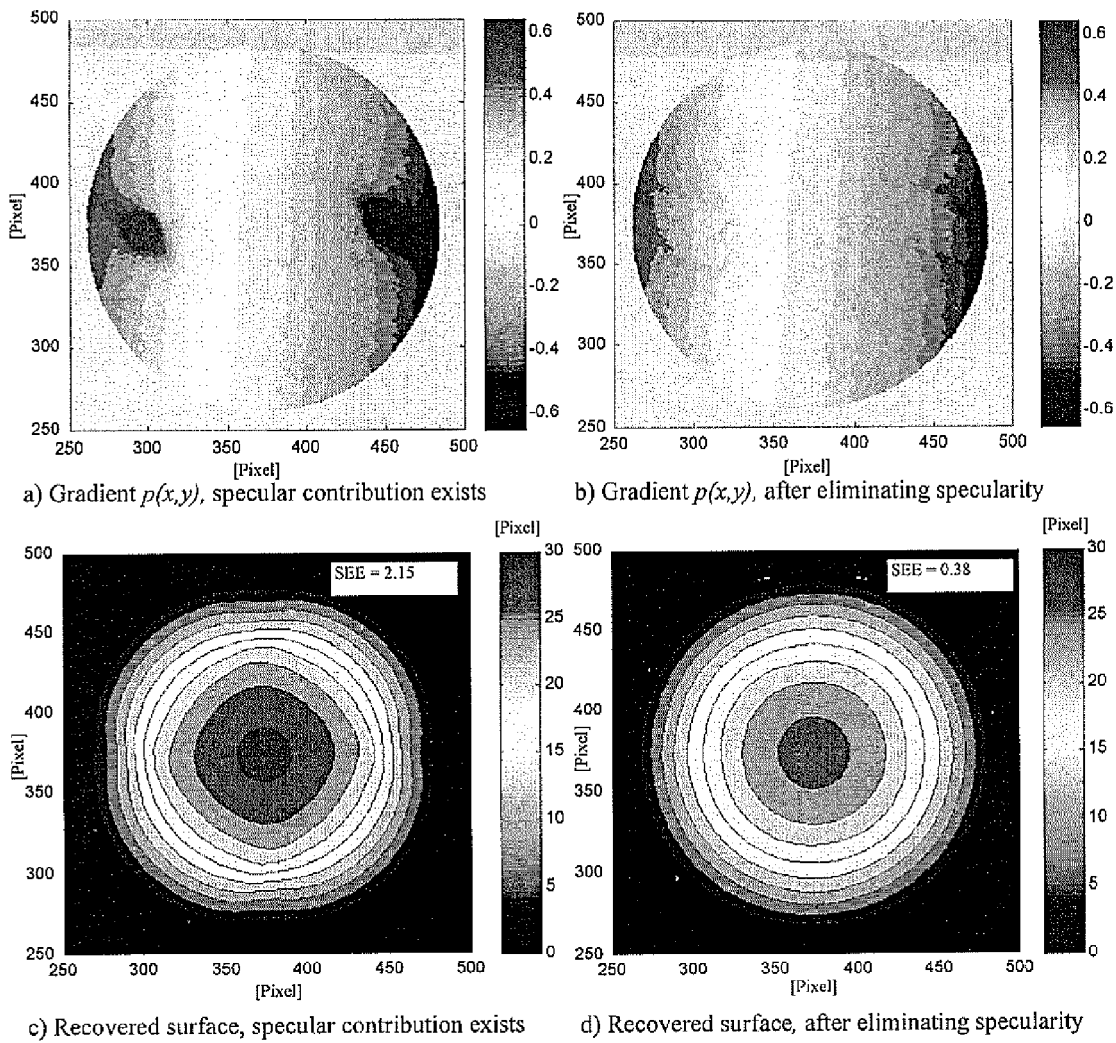
FIGS. 19a and 19b illustrate surface gradients at a threshold of 20% of the average intensity and scale 8 pixels/mm for a surface with specularity and after eliminating specularity respectively.
FIGS. 19*c* and 19*d* illustrate recovered surface contours if specular contribution exists and after eliminating specularity respectively.

FIG. 19 shows the surface gradient and the recovered surface contours for the semisphere part that has no shadow with a scale of 8 pixel/mm. The surface height us recovered using global technique. The gradient $p(x,y)$ and the surface $z(x,y)$ are shown for the specular sphere with specular contribution (FIG. 19a, c) and after eliminating specularity using a threshold of 20% of the image average intensity (FIG. 19b, d).

As shown in FIGS. 19a and b, the gradient $p(x,y)$ increases due to specular contribution with maximum value of 0.41 (from ±0.35 to ±0.76) at the pixels where the specularity existed. After eliminating the specular components, the standard error, SEE, of the estimated surface $z(x,y)$ is reduced from 2.15 to 0.38 and 0.70 pixel for 20% and 30% threshold, respectively.

The maximum difference between the recovered and the original surface is reduced from 4.75 to 0.87 and 1.53 pixels for 20% and 30% threshold, respectively. FIGS. 9b and d show that the distortion of the spherical surface due to specularity is eliminated successfully using the proposed approach.

Shadow Effect

Figure 20:
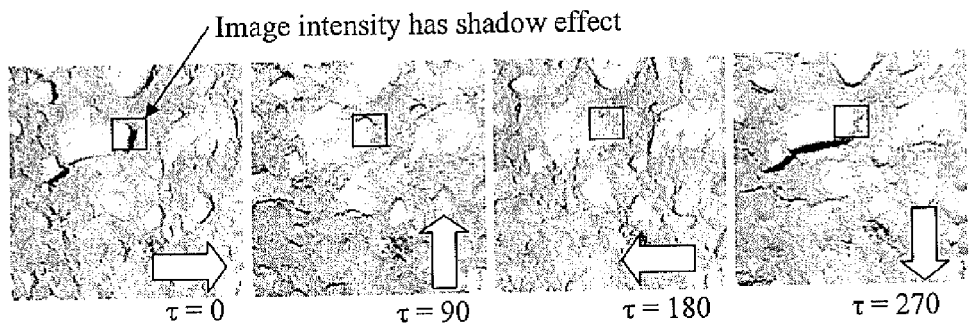
FIG. 20 illustrates images from four different lighting directions in which shadow effect is evident.

However recovery models are assumed for continuous surface with small slopes (no shadow), in pavement surfaces some shadow effects may appear. FIG. 20 shows four images with different light directions; $\tau=0°$, 90°, 180° and 270°. At $\tau=0°$, image intensity marked by the pointer appears darker because of the shadow. The surface should be recovered from the rest of the images. Similar to the steps used for detecting specular components, a threshold value is used to detect shadow effects. Intensity less than the threshold value is excluded from the analysis. A threshold value of 0.04 ($\approx$10/255) of the maximum image intensity is assumed considering image intensities are in gray scale with maximum value of 255.

Enhanced Pavement Surface Texture Recovery System

Figure 21:
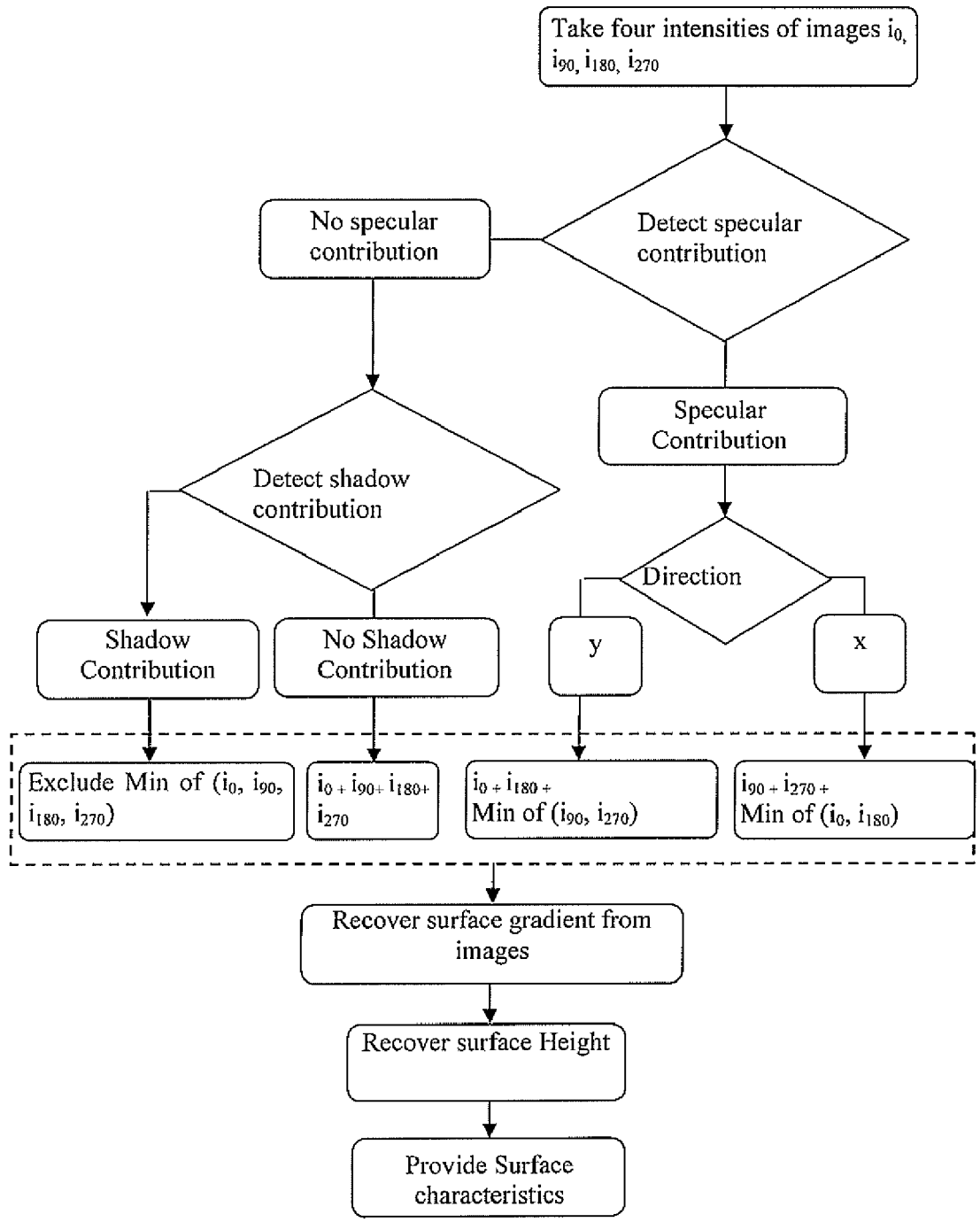
FIG. 21 is a schematic representation of a framework for pavement texture recovery from multiple images.

Surface texture recovering algorithm is enhanced so that the system detects and removes shadow and specular effects. FIG. 21 summarizes the enhanced algorithm which combined two thresholds; one for detecting specularity and the other for shadow effects. Both conditions can not exist at the same time therefore captured images are tested first against specular contribution. If there is any specularity then there is no need to test against shadow contribution. Surface gradient is computed according to four conditions; a) shadow exists; b) specularity exists in x-direction; c) specularity exists in y-direction; and d) neither shadow nor specularity exists.

Validation of Photometric Stereo Technique

Introduction

This chapter discusses laboratory experiments used to validate the proposed photometric stereo using[2] real pavement samples. System is correlated with two dimensional profiles manually measured by using a depth dial gauge.

[2] The proposed techniques has been published in the Journal of Transportation Engineering (El Gendy and Shalaby 2007C)

Manual Measurement of Surface Profiles

Figure 22:
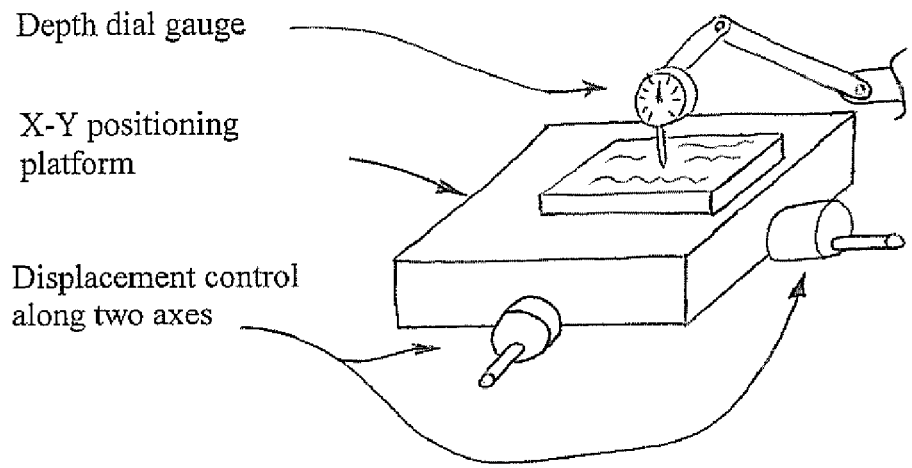
FIG. 22 is an illustration of a method and device for measuring profile depth manually.

A dial gauge is used to manually measure the surface profile depth. The gauge has an 0.01 mm vertical resolution. It is set in a fixed elevation above an x-y positioning platform with 0.00025 mm horizontal resolution (FIG. 22b). The sample is moved manually in the profile direction, and dial gauge readings are recorded at each movement step.

The ISO standard (13473-1 1997) recommends that vertical resolution be better than 0.05 mm and the sampling interval should not be more than 1 mm. For this research, the profile depth is recorded with 0.01 mm vertical resolution at 1 mm profile interval. The dial gauge has a maximum range of 10 mm. In some instances, the elevation of the dial gauge is reset when the change in the profile elevations exceeded 10 mm. In this case, a process analogous to the turning point concept in a leveling survey is used. The difference in the dial gauge positions is recorded at one location, and all the subsequent measurements are adjusted to compensate for resetting the gauge measurements.

Sample Properties

FIG. 39 lists the properties and descriptions of five types of pavement surfaces that have been tested to demonstrate the ability of the system to recover a three-dimensional surface. Samples have MPDs that ranged between 0.42 and 3.76 mm and have RMS roughnesses that ranged between 0.14 and 1.21 mm. The samples cover different pavement types and conditions e.g. worn, polished, or harsh surfaces.

Computing MPD and RMS Roughness from Surface Profile

Figure 23:
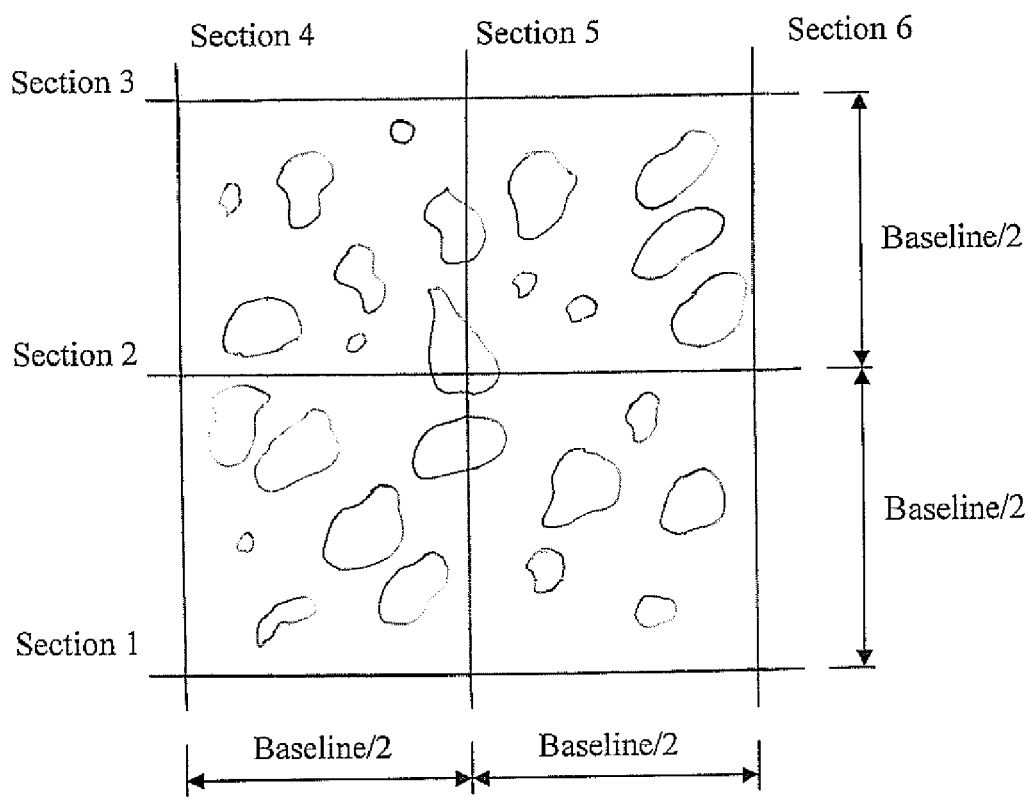
FIG. 23 is an illustration of various profile positions.

Two samples are tested from each surface type, with the exception of the smooth sample (type A1), for which only one sample is tested. A baseline of 100 mm is used for all samples except type A1. Each sample is divided into four cells, each measuring $50 \times 50$ mm$^2$. For the smooth sample, type A1, a minimum baseline of 90 mm, as recommended by the ISO standard, is used. The sample is divided into four grid cells with each cell measuring $45 \times 45$ mm$^2$. As shown in FIG. 23, six profiles are measured, three in each direction along the grid borders. The average value of the six mean depth profiles and root mean square roughnesses are reported as the MPD and the RMS roughness of the sample, respectively.

Figure 24:
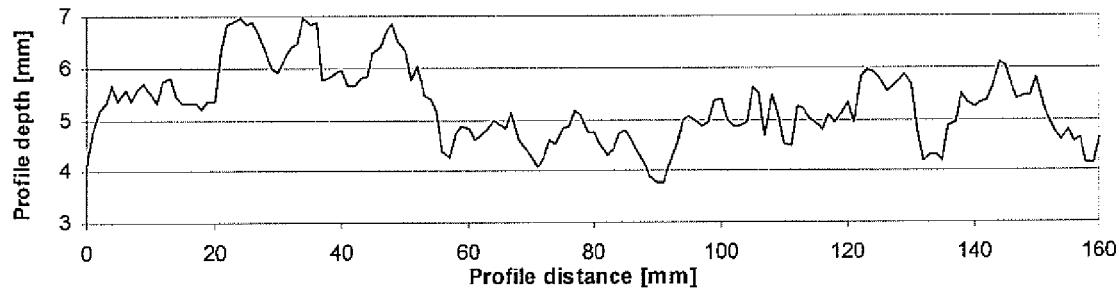
FIG. 24*a* illustrates a profile depth for Sample D1-section 3 as measured before filtering.
FIG. 24*b* illustrates a band pass filtered profile after removing wavelengths greater than or equal to 100 mm and wavelengths less than or equal to 2.5 mm.
FIG. 24*c* illustrates a computed mean profile depth for a sample baseline length of 100 mm.
Figure 24:
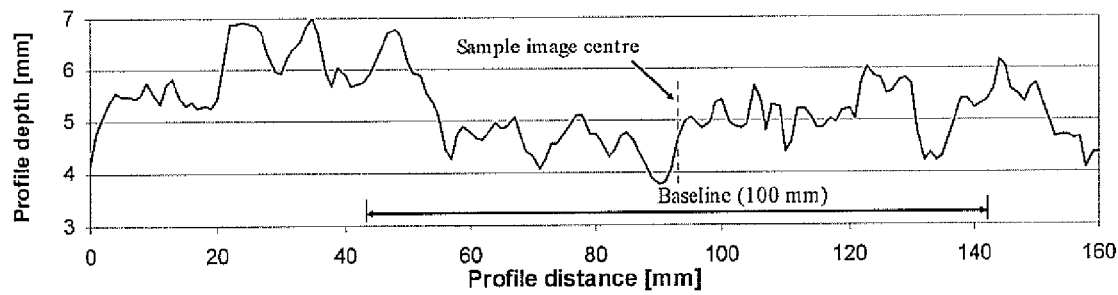
Figure 24:
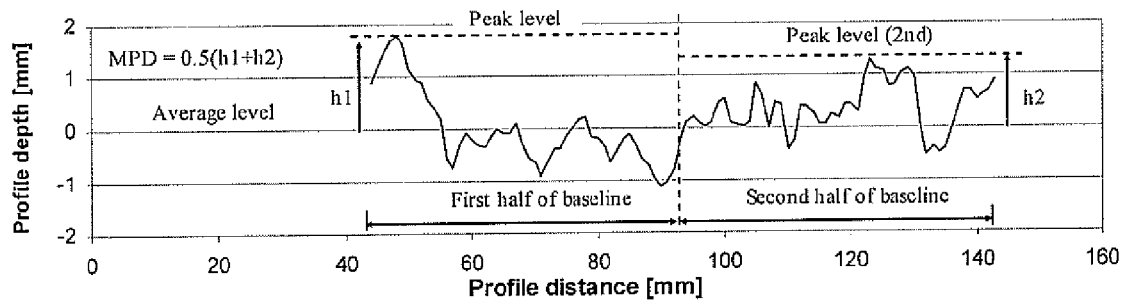

FIG. 24 illustrates the steps carried out for computing the MPD for Sample D1 at section 3. FIG. 24a shows the measured profile, and FIG. 24b shows the filtered profile after applying the band-pass filter to remove wavelengths$\geq$100 mm and wavelengths$\leq$2.5 mm. FIG. 24c shows a sample from the profile with a baseline length of 100 mm. The baseline centre coincides with the centre of the image. Similar steps are carried out for computing RMS roughness from filtered profiles.

Image-Based MPD and RMS Roughness

Figure 25:
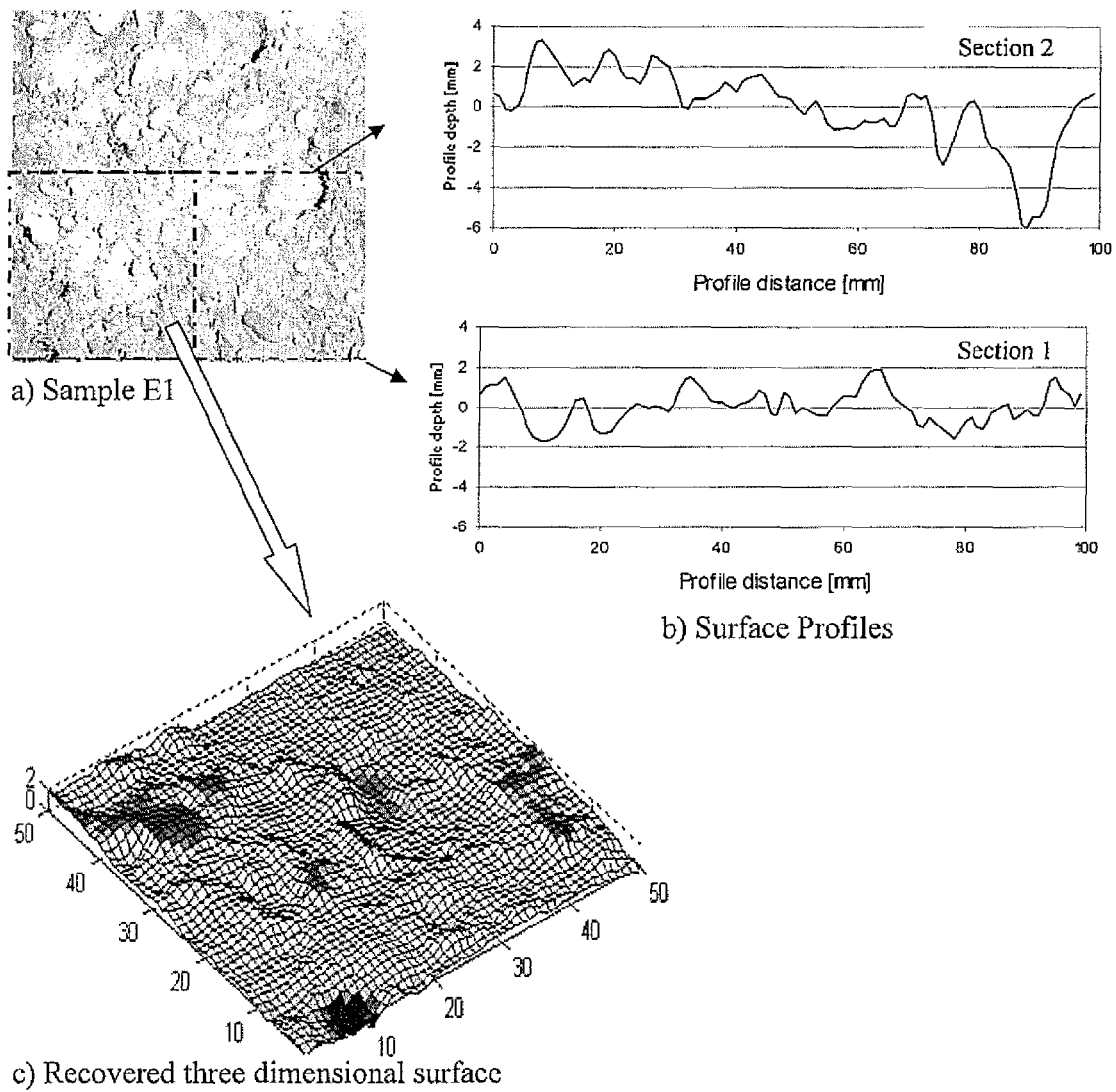
FIG. 25 is a schematic representation of pavement surface measurements.

After marking sample profile positions, each sample image is captured so that its center coincides with the image center. Each image covers an area of approximately $135 \times 105$ mm$^2$ and includes the six profiles measured manually. Images are scaled so that each pixel corresponds to $1 \times 1$ mm$^2$. The recovered surface is three-dimensional, with a base grid size of $1 \times 1$ mm$^2$. FIG. 25c shows a three-dimensional recovered surface of Pavement Sample E1. Only a quarter of the surface area is shown for illustration. From the recovered surface, mean profile depths and root mean square roughnesses are calculated to all profiles at 1 mm intervals along the x and y directions. The average values are reported as MPD and RMS roughness of the sample, respectively.

Lighting Angle

The sensitivity of the technique to the zenith angle is studied. Five zenith angles are examined: $\sigma=26°$, $28°$, $30°$, $32°$, and $34°$. In each case, changing the zenith angle (by varying the height of the lighting source from the surface and its inclination angle) is followed by a recalibration of the lighting intensity using a new adjustment coefficient matrix.

Estimated Surface Texture

RMS Roughness

Figure 26:
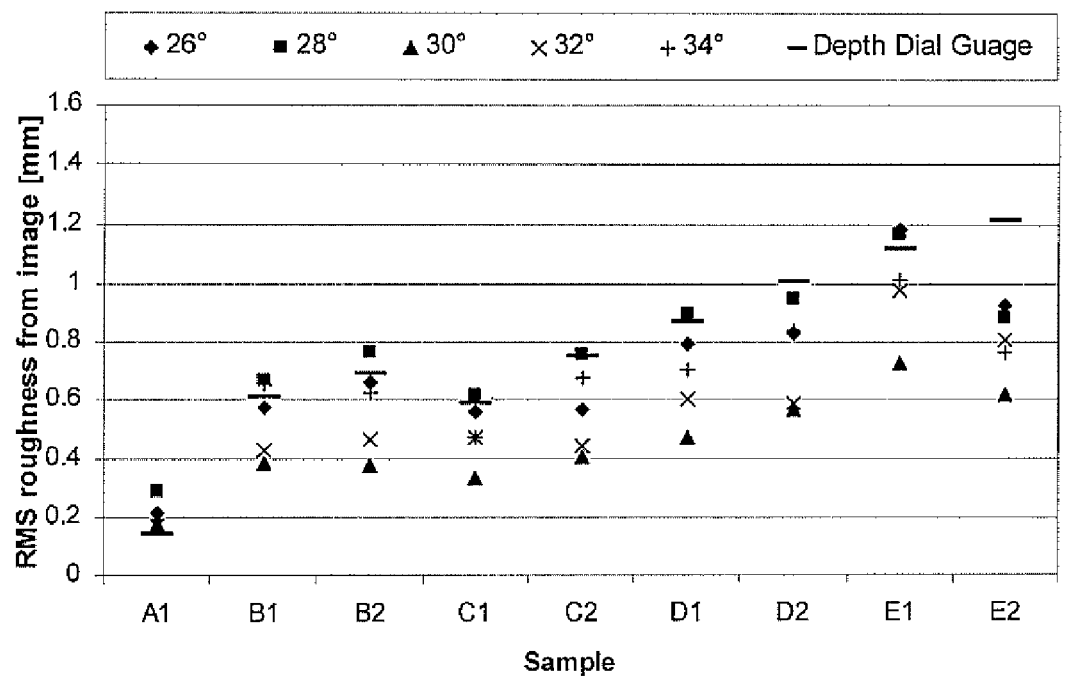
FIG. 26 and FIG. 27 are representations of image-based RMS roughness according to global integration and local integration respectively.
Figure 27:
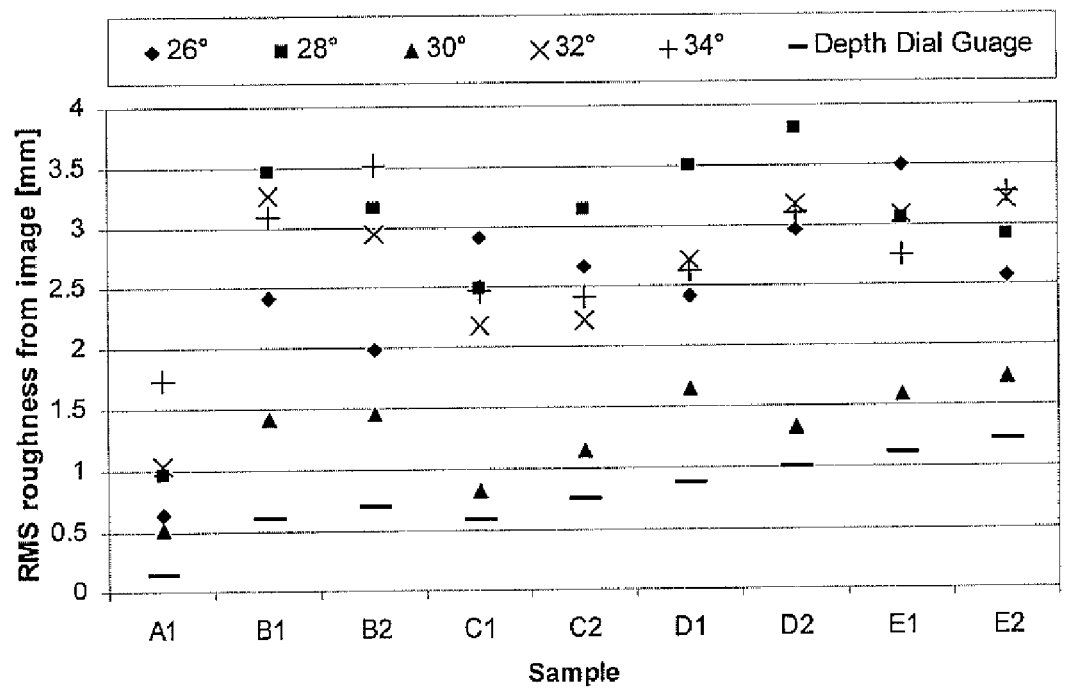

FIG. 26 shows the computed root mean square roughness, RMS, from manual readings against those computed from surfaces recovered by using global integration. While FIG. 27 shows RMS roughness computed by using local integration. In general, local integration gives RMS roughness higher than those from global integration. Also local integration gives RMS roughness higher than those from depth dial gauge depth.

Assuming a linear regression, Table 8-2 shows coefficients of determinations between the estimated RMS roughness by using the photometric stereo technique and RMS roughness computed from manual measurements. For global integration, coefficients of determinations are between $R^2=0.84$ at $\sigma=34°$ to 0.92 at $\sigma=30°$. While for local integration, coefficients of determinations are between $R^2=0.40$ at $\sigma=34°$ to 0.73 at $\sigma=30°$. The best correlation is found at zenith angle of $30°$ with a coefficient of determination of 0.92 and 0.73 for global and local integration respectively.

TABLE 8-2

Linear regression between depth dial gauge and image-based results

| Zenith angle $\sigma$ | Coefficient of determination | |
|---|---|---|
| | Local integration | Global integration |
| 26° | 0.61 | 0.87 |
| 28° | 0.49 | 0.85 |
| 30° | 0.73 | 0.92 |
| 32° | 0.65 | 0.84 |
| 34° | 0.40 | 0.84 |

When comparing the performance of the analysis of surface recovery techniques, Zang et al. (1999) found that none of the recovery algorithms has consistent performance for all images. Therefore choosing the integration method would depend on the surface shape and material.

Figure 28:
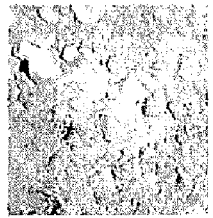
FIG. 28 is a schematic representation of a recovered pavement surface.
Figure 28:
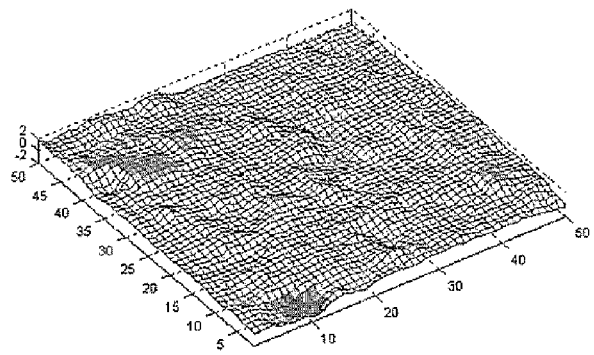
Figure 28:
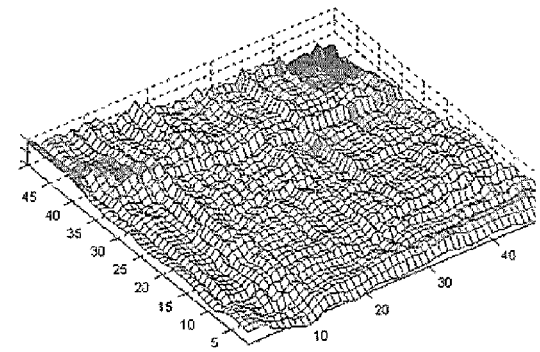

For recovering pavement surface using the proposed algorithm, global integration method shows better results over the local integration method. FIG. 28 shows the recovered surfaces of a part of Sample E1 by using global and local integration. Only a part of the sample is shown for better illustration. Surface recovered using global integration (FIG. 28b) appears smoother than that recovered using local integration (FIG. 28c). The conclusion is expected because the global integration method enforces integrability at the cost of smoothing the estimated surface.

Mean Profile Depth

Figure 29:
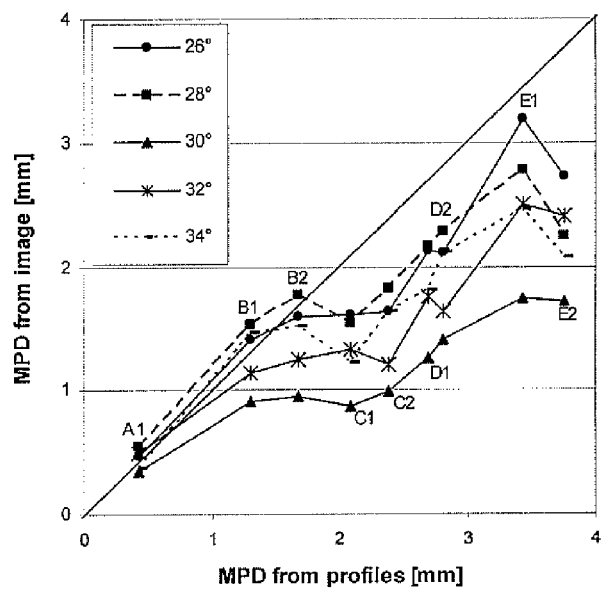
FIG. 29 is a schematic representation comparison manual and image-based mean profile depths under different zenith angles.

FIG. 29 shows the computed mean profile depth from manual readings against those computed from surfaces recovered by the photometric stereo technique. Generally, the mean profile depths computed from the photometric technique are smaller than those computed from manual measurements. This outcome is expected because the integration method used to recover depth from the surface gradient enforces integrability at the cost of smoothing the estimated surface.

Assuming a linear regression,

Table 8-3 shows the coefficients of determination between the MPD estimated by using the photometric stereo technique and the MPD computed from manual measurements. Coefficients of determination are between $R^2=0.82$ at $\sigma=34°$ and 0.92 at $\sigma=30°$. The best model is found at a zenith angle of 30° with a coefficient of determination of 0.92. The model is expressed by the following formula:

$$MPD_i = 0.41 MPD_d + 0.21 \qquad (8.1)$$

where $MPD_i$ mean profile depth from the image measurements, and $MPD_d$, mean profile depth from the depth dial gauge measurements, are expressed in millimeters. Linear regression models for other zenith angles are also listed in Table 8-3.

TABLE 8-3 linear regression between depth dial gauge and image-based results under different zenith angles

| Zenith angle σ | Linear regression model | Coefficient of determination |
|---|---|---|
| 26° | $MPD_i = 0.71 MPD_d + 0.24$ | 0.90 |
| 28° | $MPD_i = 0.56 MPD_d + 0.58$ | 0.84 |
| 30° | $MPD_i = 0.41 MPD_d + 0.21$ | 0.92 |
| 32° | $MPD_i = 0.57 MPD_d + 0.21$ | 0.90 |
| 34° | $MPD_i = 0.52 MPD_d + 0.21$ | 0.82 |

Texture Classification in Frequency Domain

Introduction

This chapter focuses on using the power spectrum of the two dimensional Fourier transform of the recovered surface as a classification indicator[3]. In most of the image processing applications in pavement research mentioned in Chapter 3, Fourier transform is applied directly to the filtered digital images. A threshold filter is used to detect the contiguous region in aggregate particle placed on a monocolor background. Also cracks in pavement surface are detected based on the difference in intensities between neighbouring pixels.

[3] The proposed indicator has been published in the CSCE 2007 Annual General Meeting & Conference (El Gendy and Shalaby 2007B)

Since the system used in this study provides a three-dimensional recovered surface of the pavement surface, Fourier transform is applied to the recovered surface heights instead of intensity images. Analyzing surface texture in frequency domain is chosen for two reasons:

The proposed photometric stereo technique recovers surface height in frequency domain, and;

In frequency domain, texture surface can be filtered so that only the frequencies of interest are considered.

Proposed Power Spectrum Indicator

Three synthetic surfaces are assumed to illustrate the proposed power spectrum indicator. Surfaces have a dimension of 48×48 units. Surfaces are assumed to have 1, 4 and 16 obstacles respectively. Obstacles with dimensions of 6×6 units and 1 unit height are distributed uniformly around the center with 6 units in-between (FIGS. 30a, 31a, and 32a).

Figure 30:
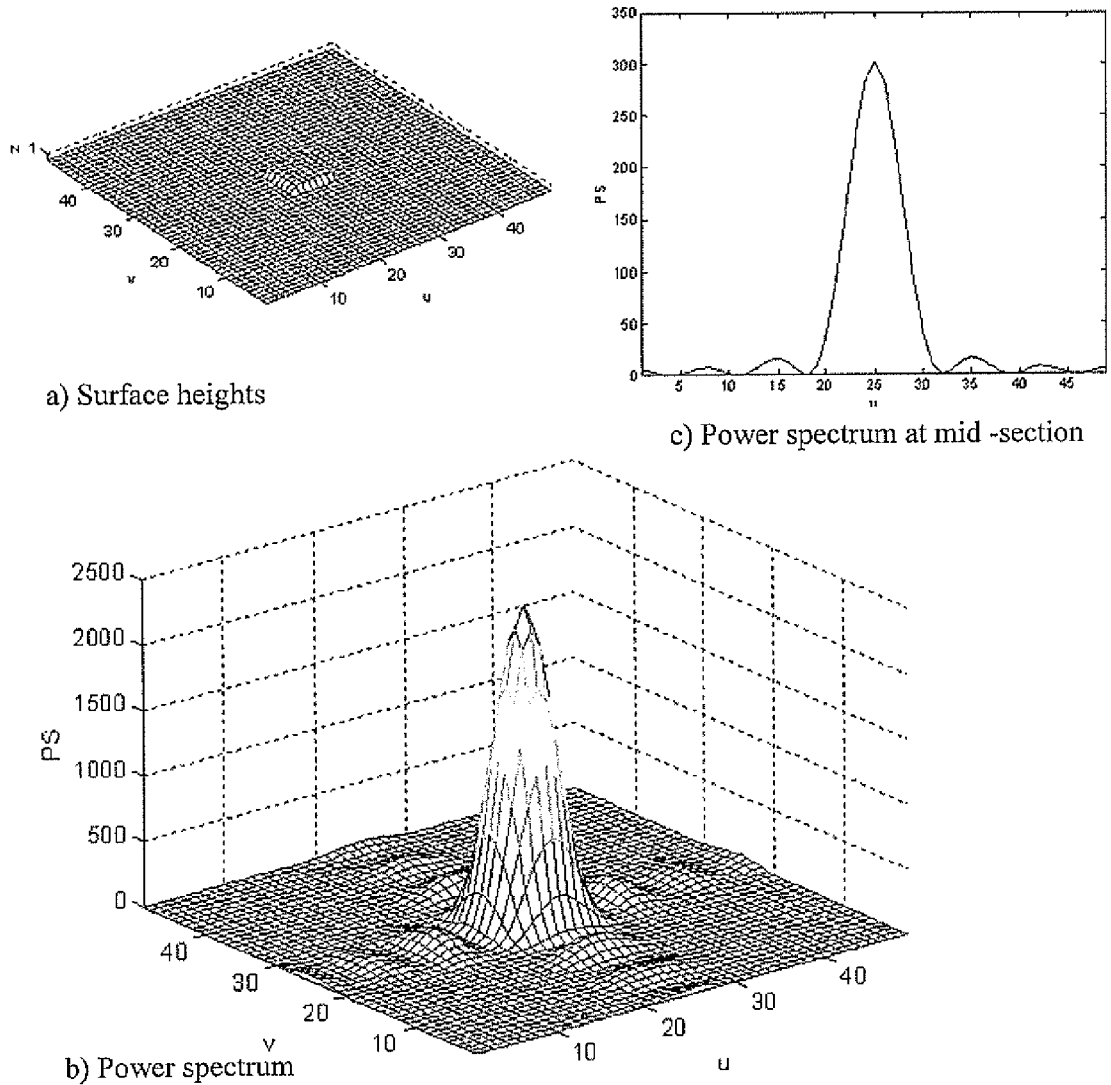
FIG. 30 is a schematic representation of power spectrum functions for one obstacle.
Figure 31:
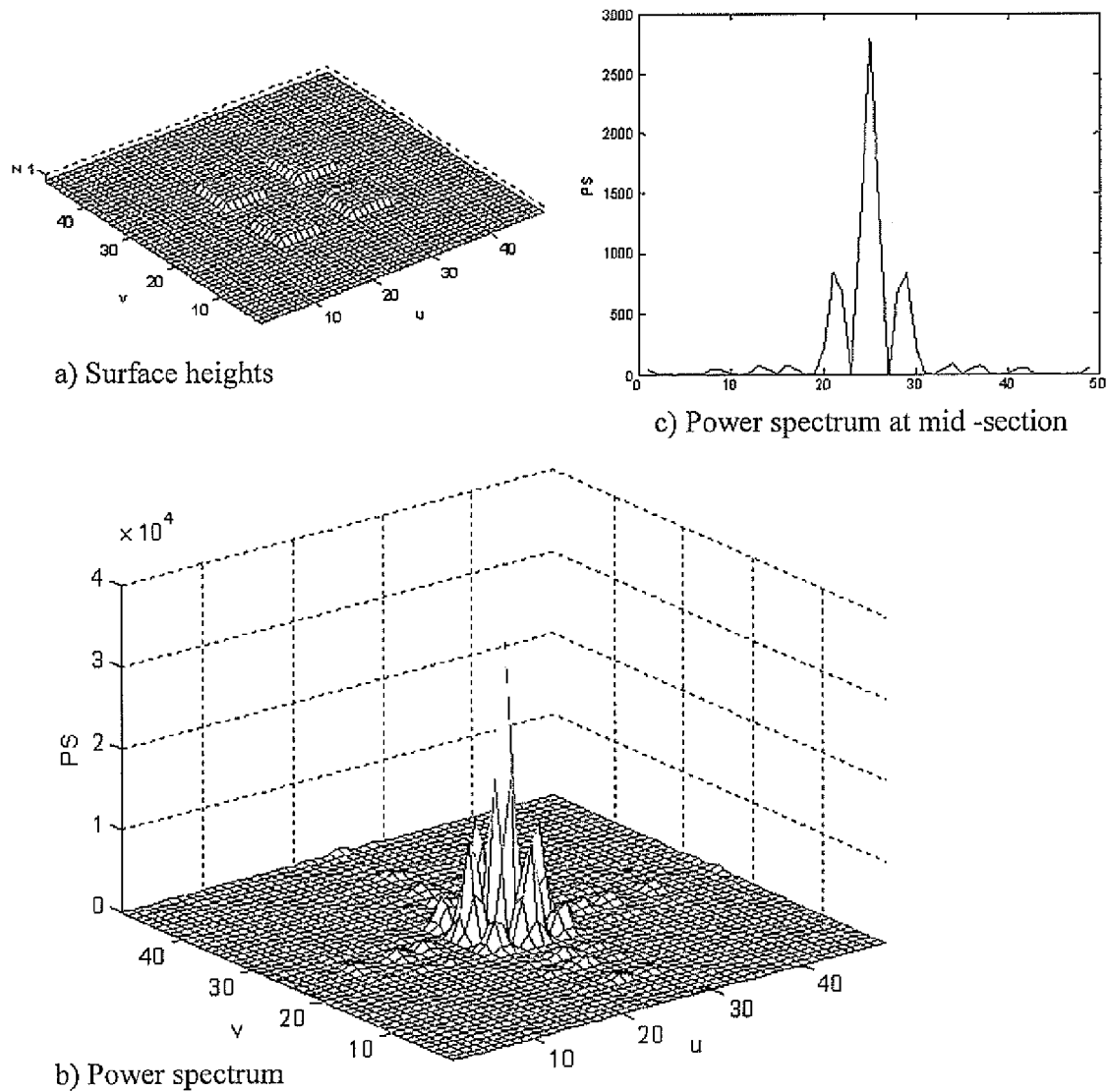
FIG. 31 is a schematic representation of power spectrum functions for four obstacles.
Figure 32:
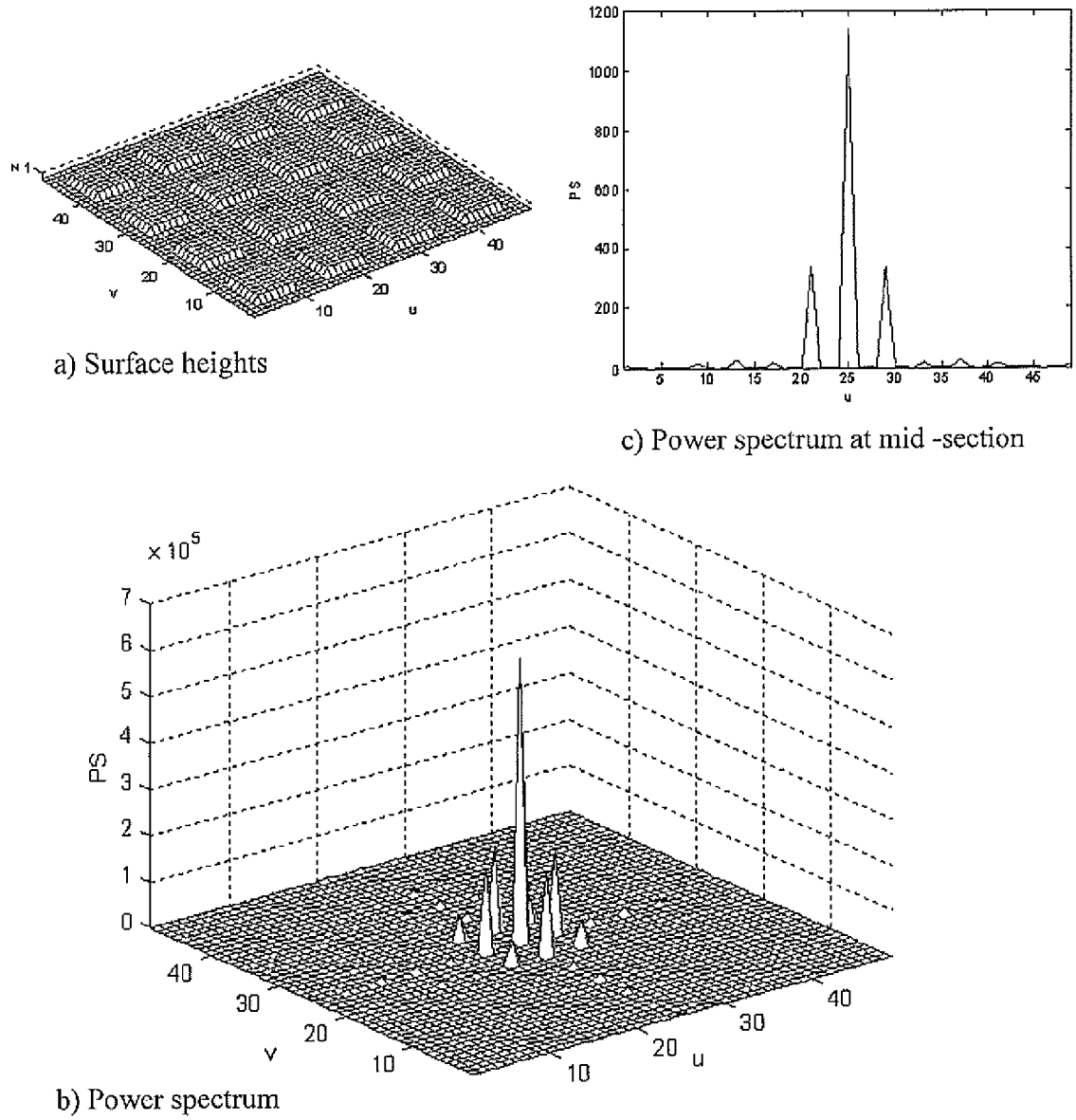
FIG. 32 is a schematic representation of power spectrum functions for sixteen obstacles.

FIGS. 30b, 31b, and 32b show the power spectrum functions for 1, 4, and 16 obstacle surfaces respectively while FIGS. 30c, 31c, and 32c show the power spectrum functions at mid-section. Power spectrum increases in values and distributes widely with the increase of obstacles number. While profile depth for these three surfaces is the same of 1 unit, the maximum power spectrum value and the distribution of the power spectrum over spatial frequencies are different and can be used as surface texture indicators. They could be replaced by the area under the power spectrum function (power spectrum energy). The total power spectrum energy, PSE, is computed as:

$$PSE = \sum_{i=1}^{n-1} \sum_{k=1}^{m-1} |Z(i,k)|^2 \qquad (9.1)$$

If image specifications are standardized, e.g. dimensions of images and condition of lighting, the total power spectrum energy can be used as texture indicator.

Estimated Texture Characteristics

Figure 33:
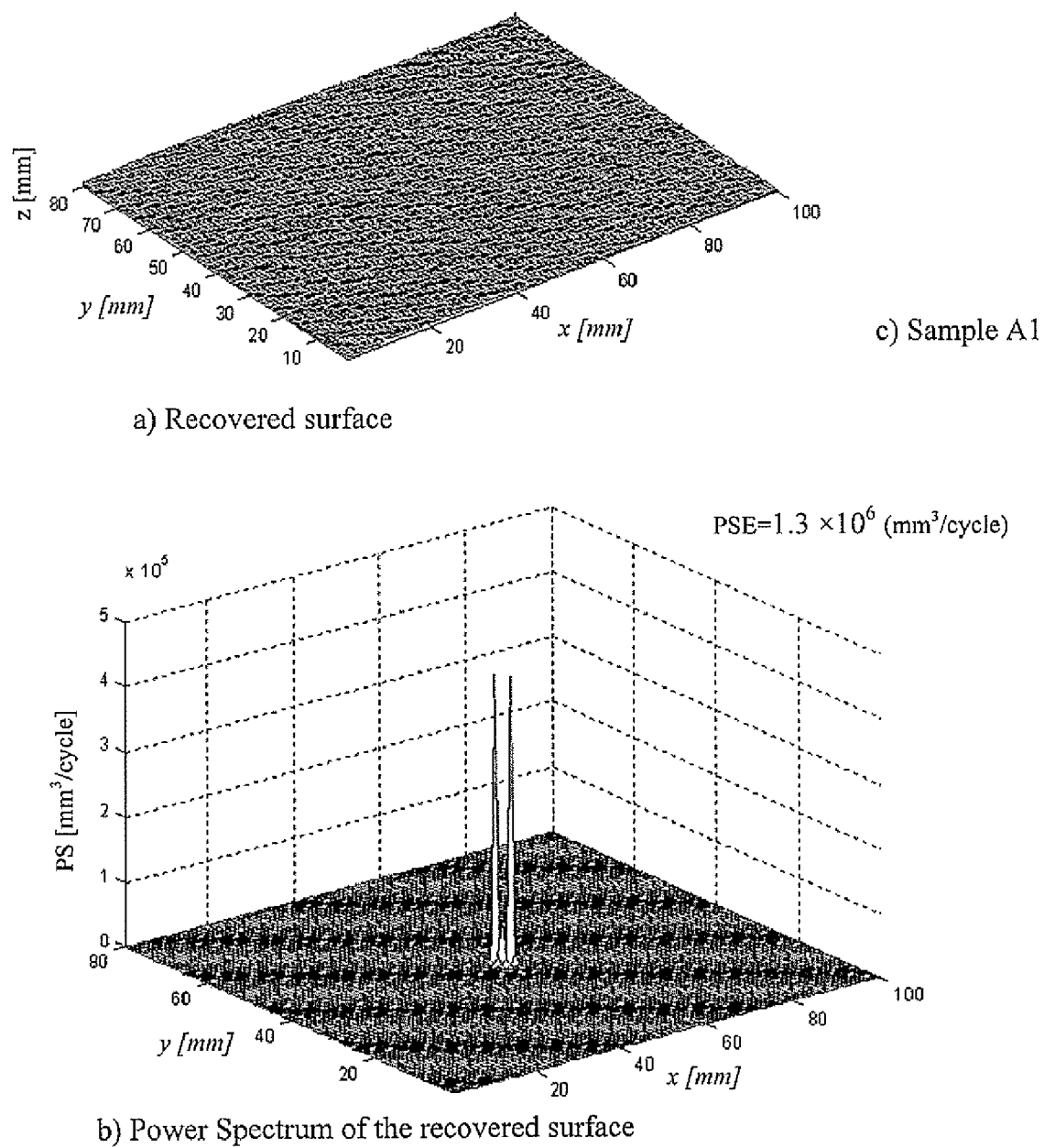
FIG. 33 is a schematic representation of a recovered surface in time and frequency domain for Sample A1.
Figure 34:
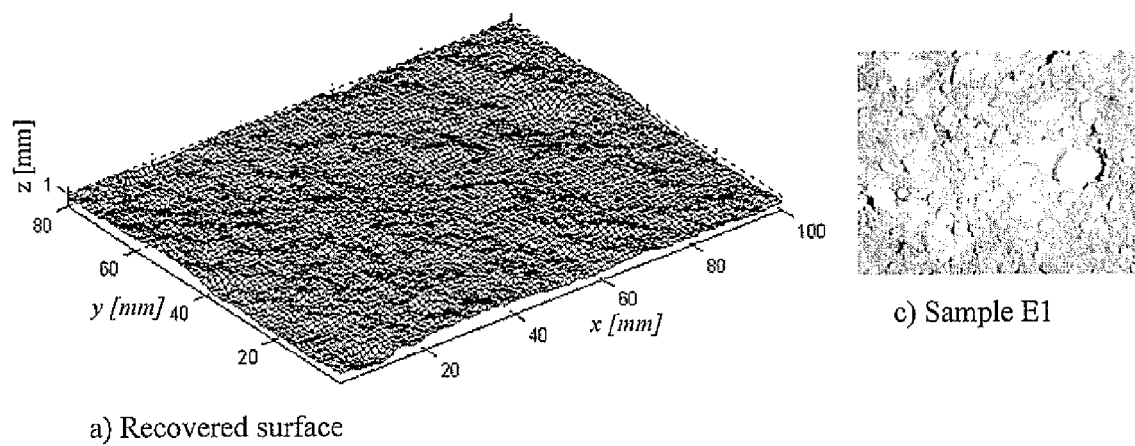
FIG. 34 is a schematic representation of a recovered surface in time and frequency domains for Sample E1.
Figure 34:
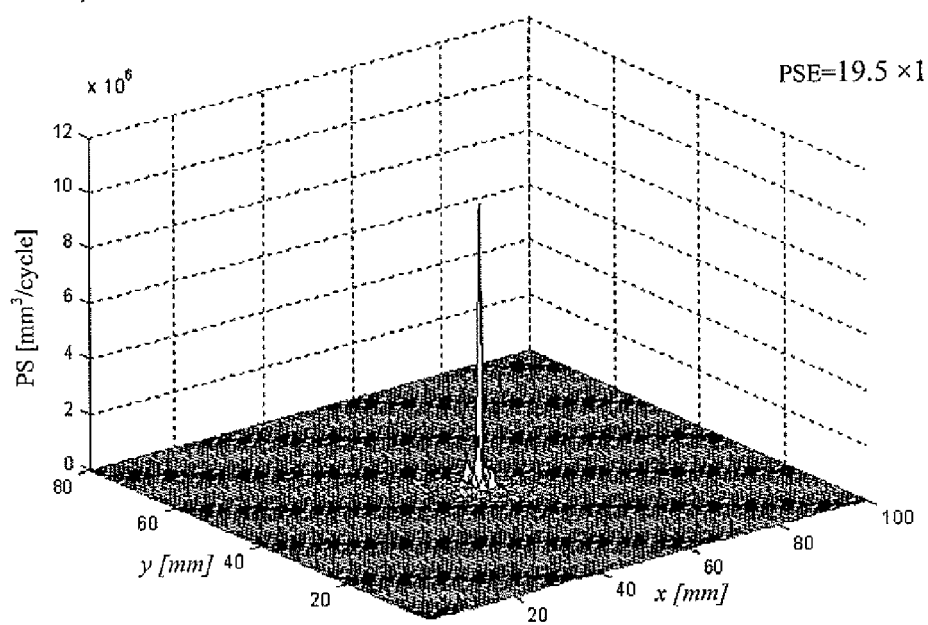

FIG. 33 shows the recovered surface and its Fourier transform of Sample A1 as an example of smooth surface. For rough surface (Sample E1), recovered surface and its power spectrum of the recovered surface are shown in FIG. 34. The smooth surface has power spectrum energy of $1.3 \times 10^6$ ($mm^2 \cdot mm/cycle$) associated with mean profile depth and root mean square roughness of 0.42 and 0.14 mm, respectively. For Sample E1, power spectrum energy is $19.5 \times 10^6$ ($mm^2 \cdot mm/cycle$) associated with mean profile depth and root mean square roughness of 3.43 and 1.11 mm, respectively.

Figure 35:
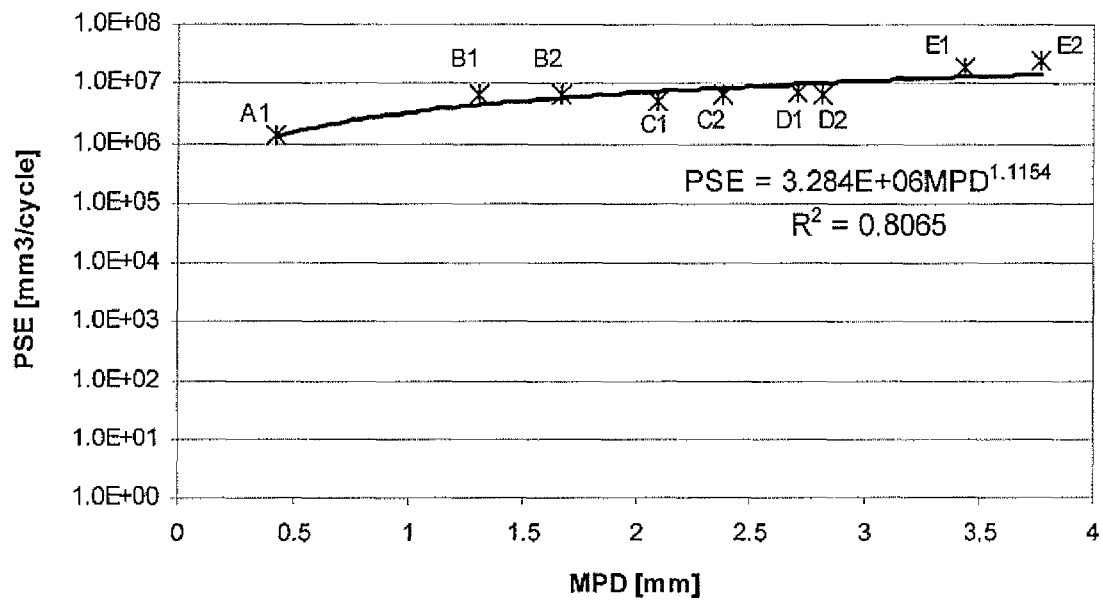
FIG. 35 graphically illustrates mean profile depths vs. a power spectrum indicator.
Figure 36:
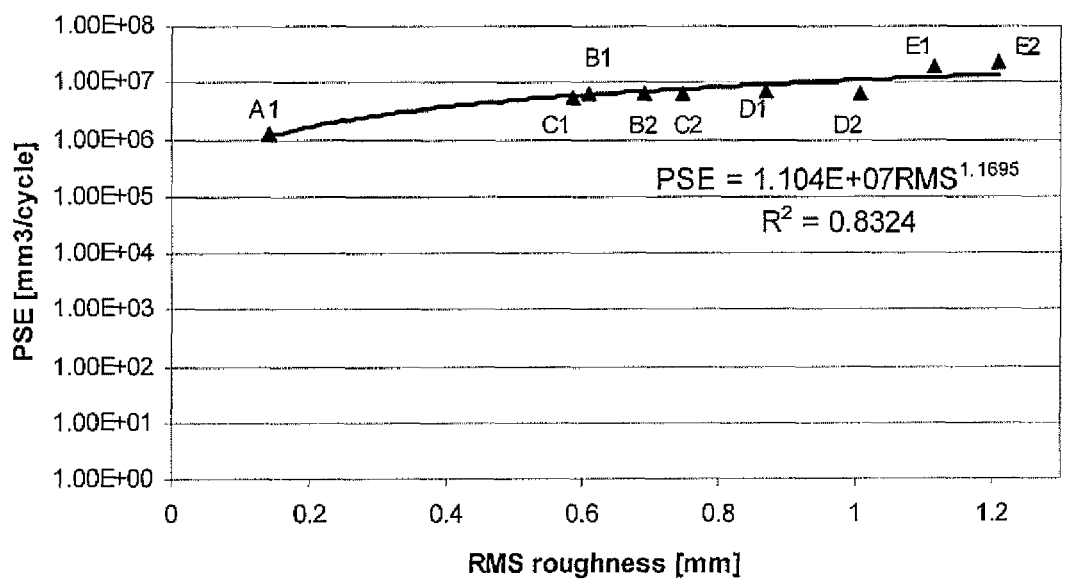
FIG. 36 graphically illustrates a root mean square roughness vs. a power spectrum indicator.
Figure 37:
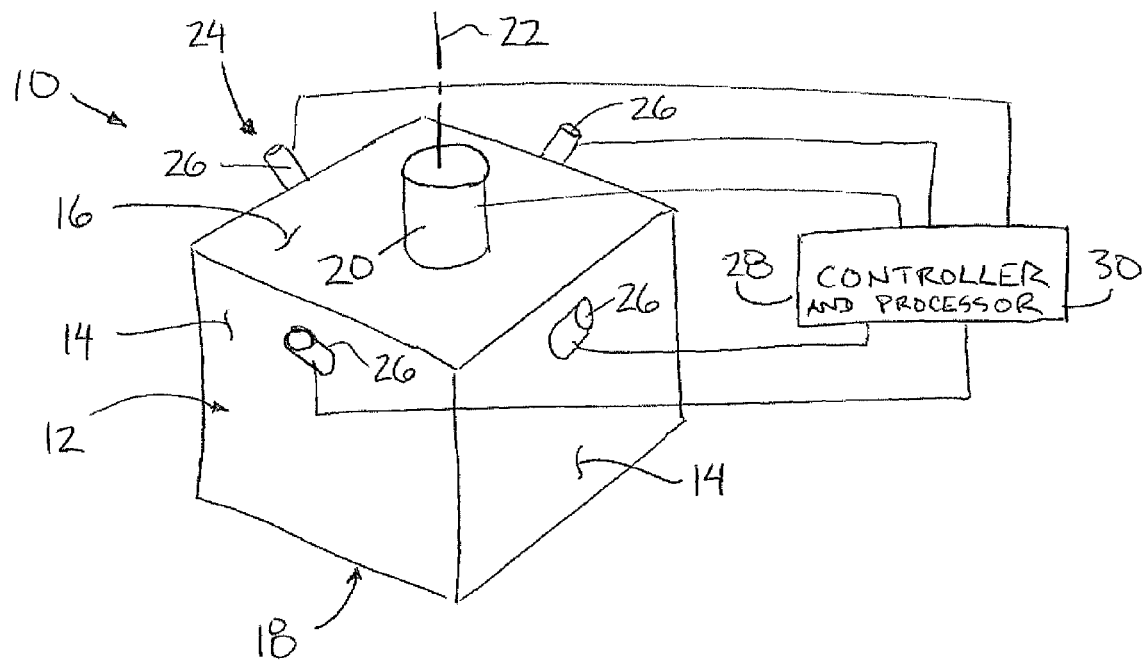
FIG. 37 is a schematic perspective view of a tool for evaluating surface texture.
Figure 38:
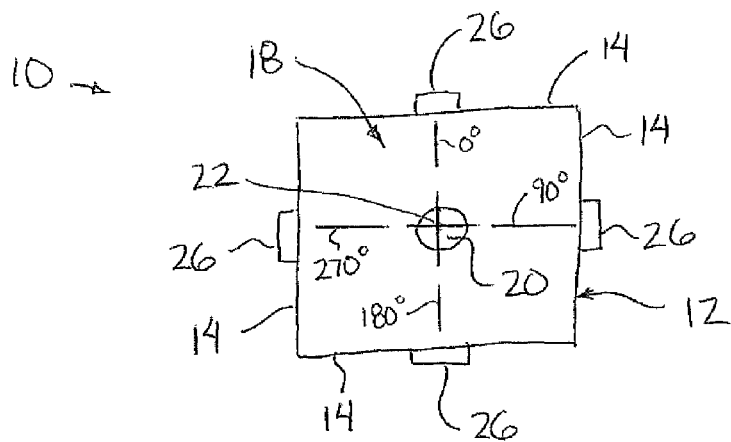
FIG. 38 is a bottom plan view of the housing of the tool according to FIG. 37.

The PSE is correlated with MPD and RMS using an exponential model. FIG. 35 shows the relationship between mean profile depth and power spectrum indicator while FIG. 36 shows the relationship between root mean square roughness and power spectrum indicator.

The mean profile depth is expressed as a function of the power spectrum indicator with a coefficient of determination $R^2=0.81$ according to the following model:

$$MPD = 1.438 \times 10^{-6} PSE^{0.8965} \qquad (9.2)$$

Similarly the root mean square roughness is expressed by the power spectrum indicator with coefficient of determination $R^2=0.83$ according to the following model:

$$RMS = 9.502 \times 10^{-7} PSE^{0.855} \qquad (9.3)$$

Conclusion

Summary and Contribution

As described herein the recovery of pavement surface texture using photometric stereo technique has been investigated. A prototype of four-source photometric stereo system has been built. The system provides a range of illumination angles from zenith angle $\sigma=25°$ to $\sigma=55°$.

A new four-source photometric stereo approach to detect specularity has been presented. Instead of calculating four surface reflectance factors and their deviation, specularity is directly detected by comparing image intensities. Results from the experimental test used to verify the approach show that a value of 20% of the average image intensity of object can be used as a threshold value. The four-source photometric stereo has been enhanced to be able to detect shadow effect.

Five types of pavement surfaces covering a range of surface textures have been tested to evaluate the system. For each sample, six surface profiles have been measured manually using a depth dial gauge. MPD and RMS roughness have been used for the comparison between manual and image processing measurements.

Surface heights are recovered from surface gradients using global and local integration methods. Test results show that pavement surface texture estimated by global integration method is more accurate than those estimated by local integration method. Also results show that $\sigma=30°$ is the optimal zenith angle (σ).

Computed RMS roughnesses using global integration are correlated with those computed from surface profiles. The coefficient of determination ranged from $R^2$=0.84 (at σ=34°) to 0.92 at (σ=30°). The best correlation has been found at a zenith angle of 30° with a coefficient of determination=0.92.

Similarly, computed MPD using photometric stereo method are correlated with those computed from surface profiles. The coefficient of determination ranged from $R^2$=0.82 (at σ=34°) to 0.92 at (σ=30°). The best model has been found at a zenith angle of 30° with a coefficient of determination=0.92. A model has been presented to estimate the mean profile depth from the recovered surface.

A new surface texture indicator, power spectrum indicator PSE, has been presented. The power spectrum indicator is computed from the energy of the Fourier transform of the surface height over an area of 100×80 $mm^2$. Results show that MPD and RMS roughness computed from filtered profiles are correlated with power spectrum energy computed from the photometric stereo system with coefficient of determination $R^2$=0.81 and 0.83 respectively. Two models to estimate MPD and RMS from the power spectrum indicator PSE have been presented.

The time required to collect measurements from one sampling location is in the order of 1-2 min. The system can be further automated to increase the productivity of data collection and analysis.

The photometric stereo measurements have been limited by the resolution of the profile interval of the manual readings, which is selected at 1 mm. Although the image-based measurements at a scale of 1 mm per pixel correlated well with manual readings, the system can capture images at a much higher resolution. Thus, the photometric stereo method can be used to evaluate smooth pavement textures (MPD<1.0 mm), which have considerable impacts on safety.

In addition to classifying surface texture using power spectrum indicator, surface recovered in frequency domain can be filtered so that noise frequencies and low frequencies are removed from the analysis.

The full recovery of the pavement surface heights in three-dimensions provides more information about surface characteristics than manual or volumetric methods. Recovering the three-dimensional pavement surface could be used for additional analysis of the surface texture characteristics such as aggregate size and distribution, ravelling, and segregation.

Since texture characteristics are correlated with friction and noise, additional research is required to study the relationship between surface texture in three-dimensions and the slipping friction coefficient of the pavement surface or noise.

Referring now to some of the accompanying figures, according to the present invention there is illustrated a surface texture evaluating tool generally indicated by reference numeral 10. The tool 10 is particularly suited for determining a surface gradient to evaluate texture of a given surface, for example pavement.

The tool 10 comprises a housing 12 including four upright walls 14 arranged in a square configuration and enclosed across a top end by a top side 16. The walls 14 and the top side 16 form an enclosure about a bottom end 18 arranged to receive the surface to be evaluated.

When the tool comprises a portable tool for in situ evaluation, the walls 14 can form a perimeter having a flat bottom about a bottom opening 18 which lies in a plane of the bottom end 18. The housing 12 is thus suitably arranged to be placed flat on a surface which is to be evaluated.

In alternative embodiments the tool may include an enclosed bottom which defines a chamber arranged to receive a sample surface deposited on the bottom wall within the chamber.

The tool includes an image capture device 20 in the form of a digital camera which is supported on the top side 16 of the housing so as to be opposite the bottom end 18. The device 20 is centrally located in the top side 16 relative to the walls 14 and is positioned along an orthogonal axis 22 which is perpendicular to the plane of the bottom opening locating the target surface and centrally located between the walls 14. The camera forming the image capture device 20 is oriented to face in the direction of the orthogonal axis 22 from the top side 16 towards the bottom opening 18 for capturing an image of the surface upon which the tool rests through the bottom opening 18.

A light source 24 is supported on the housing and is arranged to project light in a lighting direction generally downwardly onto the surface to be evaluated through the bottom opening 18 from a plurality of positions spaced radially outwardly from the orthogonal axis 22. The housing defines four light source positions 26 each of which are arranged to receive light from the light source 24 and project the light therefrom in a respective light direction from the light source position 26 at the top side 16 of the housing downwardly and inwardly at an angle of inclination in the order of 30 degrees relative to the orthogonal axis 22.

The light source positions 26 are circumferentially spaced about the orthogonal axis 22 at 90 degree intervals relative to one another so as to define a laterally opposed pair of the light source positions 26 diametrically opposite and 180 degrees apart from one another and a longitudinally opposed pair of the light source positions 26 which are also diametrically opposed and 180 degrees offset from one another about the orthogonal axis.

Light is only projected from one of the light source positions 26 at any given time to project downwardly and inwardly towards the surface at the bottom opening and towards the orthogonal axis 22 which is centrally located. In a preferred embodiment the light source 24 provides light from a common generator of light to each of the light source positions so that each light source position 26 projects light therefrom of constant intensity relative to the other positions.

A controller 28 is provided which operates direction of the light source 24 to the light source positions 26 and which operates capturing of images by the image capture device 20. The controller cycles the light source positions 26 and captures one image corresponding to light from each of the four light source positions 26 so that a total of four images are captured and recorded by the controller. When any one image is taken, light is projected only from the designated light source position 26 while the walls 14 and top side 16 serve to shield and block all other ambient light from reaching the surface being evaluated.

A computer processor 30 processes the captured images and determines if a specularity condition exists among the captured images prior to calculating a surface gradient of the surface. The resulting surface gradient can then be stored or displayed to the user by the computer processor 30.

The computer processor 30 function is illustrated in a flow chart in FIG. 21. As shown the surface is illuminated from each one of the light source positions 26 sequentially in which one image of the surface is captured for each of the light source positions. An illumination intensity is recorded for each image comprising an average intensity value of the image which averages a field of varying illumination and reflection intensities and the resulting average intensities are compared directly with the intensities of the other images in order to determine if error resulting from specularity is present. In particular the processor sums the intensity of the images corresponding to illumination from laterally opposed light source positions 26 and also sums the intensity of the images associated with the longitudinally opposed pair of light source positions 26. If either summation is greater than the other by a prescribed threshold amount, a specularity condition is determined to be present. The threshold amount preferably comprises approximately 20 percent of the summation of an opposed pair of intensities being compared to.

By comparing summations of intensities of the images with diametrically opposed lighting configurations a more simplified calculation can be performed to determine if a specularity condition exists so that more complex prior art algorithms can be avoided. If a specularity condition exists, the processor subsequently calculates the surface gradient by using the intensity values from only three of the images. The intensities of the image which is rejected from the surface gradient calculation comprises the image having the highest intensity among the summation of image intensities of opposed lighting configuration which is the highest.

If there is concern for an error due to a shadow being present in one of the images, the processor can also evaluate if there is a shadow condition which exists. The shadow condition is determined by comparing the average intensity of each of the four images to a prescribed threshold. The prescribed threshold comprises a percentage of a maximum intensity among the intensities of the images, which is 4% in the preferred embodiment. The shadow condition exists if intensity of one of the images is less than the prescribed threshold. In this instance, the processor determines which three images of the four images are least affected by shadow by excluding the image having lowest intensity and the surface gradient is determined using the three images remaining. If no shadow condition exists and no specularity condition exists, the surface gradient is determined by the processor using all four of the images.

In some embodiments the tool may comprise an automated device which is simply positioned adjacent a target surface so that the surface is in the plane of the bottom opening or a sample of the surface is placed in the bottom of the chamber of the housing at which point the computer processor automatically directs the sequential illumination of the surface from the four light source positions while capturing an image of the surface in each of the four lighting positions. Once the images are captured, the processor can then automatically determine if there exists either a specularity condition or a shadow condition and then calculate the appropriate surface gradient to be either stored in memory or displayed to the user.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

Any references referred to above and in the following are incorporated herein by reference.

REFERENCES

1. Abbas, A., Kutay, M. E., Azari, H. and Rasmussen, R., "Three-Dimensional Surface Texture Characterization of Portland Cement Concrete Pavements," Computer-Aided Civil and Infrastructure Engineering Volume 22, 2007, pp. 197-209.
2. Abe, H., Tamai, A., Henry, J. and Wambold, J, "Measurement of Pavement Macrotexture with Circular Texture Meter," Transportation Research Record 1764, TRB, National Research Council, Washington, D.C., 2001, pp. 201-209.
3. American Concrete Pavement Association, "Concrete Pavement Surface Texture," a special report in Concrete Pavement Technology and Research, SR902P, 2000.
4. American Society for Testing and Materials, Standards Designations, "Road and Paving Materials; Vehicle-Pavement Systems," in the Annual Book of ASTM Standards, Volume 04.03, 2005.
5. Balmer, G. G. (1978). "Pavement Texture: Its Significance and Development." *Transportation Research Record: J. of the Transportation Research Board*, 666, 1-6.
6. Bennett, Jean M., and Mattsson, L., "Introduction to Surface Roughness and Scattering," Optical Society of America, 2 edition, 1999.
7. Britton, S. C., Ledbetter, W. B., and Gallaway, B. M., "Estimation of Skid Numbers from Surface Texture Parameters in the Rational Design of Standard Reference Pavements for Test Equipment Calibration," Journal of Testing and Evaluation, JTEVA, Vol. 2, No. 2, March 1974, pp. 73-83.
8. Cheng, H. D., Wang, J., Hu, Y. G., Shi, X. J., and Chen X. W., "Novel Approach to Pavement Cracking Detection Based on Neural Network," Transportation Research Record 1764, TRB, National Research Council. Washington, D.C., 2001. pp. 119-126.
9. Coleman, E. N. Jr. and Jain, R. "Obtaining 3-Dimensional Shape of Textured and Specular Surface Using Four-Source Photometry," Computer Graphics and Image Processing, Vol. 18, 1982, pp. 309-328.
10. Drbohlav, O. and Chantler, M., "On Optimal Light Configurations in Photometric Stereo," in ICCV 2005: Proceedings of the 10th IEEE International Conference on Computer Vision, vol. II, pp. 1707-1712, Beijing, China, 2005.
11. El Gendy, A and Shalaby, A. "Improved Specularity Detection relying on a Photometric Stereo Technique," in Graphics, Vision, and Image Processing, GVIP, The International Congress for Global Science and Technology, (ICGST), Volume 6, No. 4, 2007A.
12. El Gendy, A and Shalaby, A. "Pavement Texture Classification Using Two Dimensional Fourier Transform of Image-Based Recovered Surface," in the CSCE 2007 Annual General Meeting & Conference, Yellowknife, Canada, Jun. 6-9, 2007B.
13. El Gendy, A and Shalaby, A. "Mean Profile Depth of Pavement Surface Macrotexture Using Photometric Stereo Techniques," accepted for publishing in the Journal of Transportation Engineering, American Society of Civil Engineers (ASCE), Vol. 133, No. 1, July 2007C.
14. Ergun, M., Lyinam, S., and Lyinam, A. F., "Prediction of Road Surface Friction Coefficient Using Only Macro- and Microtexture Measurements," Journal of Transportation Engineering, Vol. 131, No. 4, Apr. 1, 2005, pp. 311-319.
15. Fletcher, T., Chandan, C., Masad, E., and Sivakumar, K. "Measurements of Aggregate Texture and its Influence on HMA Permanent Deformation," Transportation Research Record: TRB 2002 Annual Meeting CD-ROM, National Research Council, Washington D.C., 2002.
16. Fletcher, T., Chandan, C., Masad, E., and Sivakumar, K. "Aggregate Imaging System (AIMS) for Characterizing the Shape of Fine and Coarse Aggregates," Transportation Research Record: TRB 2003 Annual Meeting CD-ROM, National Research Council, Washington D.C., 2003.
17. Flintsch, G. W., de León, E., McGhee, K., and Al-Qadi, I. "Pavement Surface Macrotexture Measurement and Application,"." Transportation Research Record: J. of the Transportation Research Board, 1860, 168-177.
18. Frankot, R. T. and Chellappa, R., "A Method for Enforcing Integrability in Shape from Shading Algorithms," IEEE Transactions on Pattern Analysis and Machine Intelligence, Vol. 10, No. 4, July 1988, pp. 439-451
19. Gullón, C. a, "Height recovery of rough surfaces from intensity images," PhD thesis, Heriot-Watt University, Edinburgh, Scotland, February 2003, 214 p.
20. Gransberg, D., Karaca, I., and Burketi, W., "Quantifying Seal Coat Surface Condition Using Digital Image Processing Based on Information Theory," The International Journal of Pavement Engineering, 2002 Vol. 3 (4), pp. 197-205.
21. Gransberg, D., Pidwerbesky, B. Stemprok, R., and Waters, J. "Measuring Chip Seal Texture with Digital Imagery," in Surface Friction International Conference, Christchurch, New Zealand, May 205.
22. Healey, G. and Jain, R. "Depth recovery from surface normals," Proceeding $7^{th}$ international conference on pattern recognition, IEEE, 1984, pp. 894-896.
23. Horn, B. K. P., "Understanding Image Intensities," Artificial Intelligence, Vol. 8, 1977, pp. 201-231.
24. Horn, B. K. P. and Brooks, M. J., "The variational approach to shape from shading," Computer Vision, Graphics, and Image Processing, Vol. 33, 1986, pp. 174-208.
25. Horn, B. K. P., "Height and gradient from shading," International Journal of Computer Vision, 5, 1990, pp. 37-75.
26. Hryciw, R. D. and Raschke, S. A., "Development of Computer Vision Technique for in Situ Soil Characterization," Transportation Research Record 1526, TRB, National Research Council. Washington, D.C., 1996. pp. 86-97.
27. Ikeuchi, K., "Determining Surface Orientations of Specular Surfaces by Using the Photometric Stereo Method," IEEE Transactions on Pattern Analysis and Machine Intelligence, Vol. PAMI-3, No. 6, November 1981, pp. 661-669.
28. International Organization for Standardization, "Characterization of Pavement Texture by Use of Surface Profiles," Part 1: Determination of Mean Profile Depth, ISO 13473-1, 1997.
29. International Organization for Standardization, "GPS-Surface texture: Profile method," Terms, definitions and surface texture parameters, ISO 4287, 1997.
30. Klein, P., Hamet, J. and Anfosso-Lédée, F. (2004). "An envelopment procedure for tire/road contact." The $5^{th}$ Symposium on Pavement Surface Characteristics, (CD-Rom), Toronto, Canada.
31. Klette, R. and Schlüns, K. "Height data from gradient fields," Proceedings of SPIE (the international Society for Optical Engineering) on Machine Vision Applications, Architectures, and Systems Integration, Boston, Mass., USA. 2908 (1996) pp. 204-215.
32. Kuo, C.-Y., Frost, J. D., Lai, J. S., and Wang, L. B., "Three-Dimensional Image Analysis of Aggregate Particles from Orthogonal Projections," Transportation Research Record 1526, TRB, National Research Council. Washington, D.C., 1996. pp. 98-103.
33. Kuo, C.-Y., and Freeman, R. B., "Imaging Indexes for Quantification of Shape Angularity, and Surface Texture of Aggregates," Transportation Research Record 1721, TRB, National Research Council. Washington, D.C., 2000. pp. 57-65.
34. Lee, M. K. and Kuo, C., "Surface reconstruction from photometric stereo images," Optical Society of America, Vol. 10, No. 5, May 1993, pp. 855-867.
35. Leu, M. C. and Henry, J. J., "Prediction of Skid Resistance as a Function of Speed from Pavement Texture," Transportation Research Record 666, TRB, National Research Council. Washington, D.C., 1978. pp. 7-13.
36. Lin, Chin-Teng, Cheng, W, and Liang, S., "A 3-D Surface Reconstruction Approach Based on Postnonlinear ICA Model," IEEE Transaction on Neural Networks, Vol. 16, No. 6, November 2005, pp. 1638-1650.
37. Masad, E., Button, J. W., and Papagiannakis, T., "Fine-Aggregate Angularity: Automated Image Analysis Approach," Transportation Research Record 1721, TRB, National Research Council. Washington, D.C., 2000. pp. 66-72.
38. Masad, E., Olcott, D., White, T., and Tashman, L., "Correlation of Fine Aggregate Imaging Shape Indexes with Asphalt Mixture Performance," Transportation Research Record 1757, TRB, National Research Council. Washington, D.C., 2001. pp. 148-156.
39. McGunnigle, G., "The Classification of Textured Surfaces Under Varying Illuminant Direction," PhD thesis, Heriot-Watt University, Edinburgh, Scotland, June 1998, 268 p.
40. Nayar, S. K., Ikeuchi, K., and Kanade, T., "Determining shape and reflectance of hybrid surface by photometric sampling," IEEE Transactions Robotics Automation, Vol. 6 No. 4, August 1990, pp. 418-431.
41. Nayar, S. K., Ikeuchi, K., and Kanade, T., "Surface Reflection: Physical and Geometrical Perspectives," IEEE Transactions on Pattern Analysis and Machine Intelligence, Vol. 13 No. 7, July 1991, pp. 611-634.
42. Rao, C., and Tutumluer, E., "Determination of Volume of Aggregates: New Image-Analysis Approach," Transportation Research Record 1721, TRB, National Research Council. Washington, D.C., 2000. pp. 73-80.
43. Schonfeld, R. "Photo-Interpretation of Skid Resistance," Highway Research Record: No. 311 "Pavement Slipperiness, Roughness, and Condition Evaluation", National Research Council, Washington D.C., 1970.
44. Spence, A. D. and Chantler, M. J., "Optimal illumination for three-image photometric stereo using sensitivity analysis," IEE Proceedings in Vision, Image and Signal Processing, Volume: 153, Issue: 2, April 2006, pp: 149-159.
45. Woodham, Robert J., "Photometric method for determining surface orientation from multiple images," Optical Engineering, Vol. 19 No. 1, 1980, pp. 139-144.
46. Wu, Z. and Li, L., "A line-Integration Based Method for Depth Recovery from Surface Normals," Computer vision, Graphics, and Image Processing, Vol. 43, 1988, pp. 53-66.
47. Wei, T. and Klette, R., "Height from Gradient with Surface Curvature and Area Constraints," proceeding of the $3^{rd}$ Indian Conference on Computer Vision Graphics and Image Processing, ICVGIP 2002 (http://www.ee.iitb.ac.in/~icvgip/PAPERS/204.pdf).
48. Zhang, R., Tsai, P., Cryer, J. E. and Shah, M. "Shape from Shading: A Survey," IEEE Transactions on Pattern Analysis and Machine Intelligence, Vol. 21, No. 8, August 1999, pp. 690-706.

The invention claimed is:

1. A method of evaluating texture of a surface, the method comprising:

providing an image capturing device arranged to capture an image;

providing a source of light arranged to project light in a lighting direction;

locating the image capturing device along an orthogonal axis extending perpendicularly from the surface and facing the surface in a direction of the orthogonal axis so as to be arranged to capture an image of the surface;

sequentially projecting light onto the surface from each of four light source positions spaced circumferentially about the orthogonal axis;

arranging the lighting direction to be at a constant angle of inclination relative to the orthogonal axis in each of the four light source positions;

arranging an intensity of the projected light to be constant in each of the four light source positions;

capturing four images of the surface using the image capturing device in which the surface is illuminated by the light source from a respective one of the four lighting positions when each of the four images are captured;

determining if a specularity condition exists in one of the four images by comparing intensities of the images directly with one another;

if a specularity condition exists:
i) determining three images of the four images which are least affected by specularity; and
ii) determining a surface gradient of the surface using the three images.

2. The method according to claim 1 including determining if a specularity condition exists by comparing relative intensities of the four images to a prescribed threshold.

3. The method according to claim 1 including arranging the four light source positions to comprise two pairs of diametrically opposed positions and determining if a specularity condition exists by comparing intensities of the images of one of the pairs of light source positions to intensities of the images of the other pair of light source positions.

4. The method according to claim 1 including arranging the four light source positions to comprise two pairs of diametrically opposed positions and determining if a specularity condition exists by calculating a difference between a summation of intensities of the images of one of the pairs of light source positions and a summation of intensities of the images of the other pair of light source positions and comparing the difference to a prescribed threshold.

5. The method according to claim 4 including arranging the threshold to comprise approximately 20% of a magnitude of the values being compared.

6. The method according to claim 1 including, if no specularity condition exists, determining a surface gradient of the surface using all four of the images.

7. The method according to claim 1 including determining three images of the four images which are least affected by specularity by excluding the image having greatest intensity.

8. The method according to claim 1 including arranging the four light source positions to comprise two pairs of diametrically opposed positions and determining three images of the four images which are least affected by specularity by excluding the image having the greatest intensity among the images of one pair of lighting positions having the greatest sum of intensity.

9. The method according to claim 1 including locating the four light source positions circumferentially about the orthogonal axis spaced at 90 degree intervals relative to one another.

10. The method according to claim 1 including orienting the angle of inclination of the lighting direction to be between 20 degrees and 55 degrees relative to the orthogonal axis.

11. The method according to claim 1 including orienting the angle of inclination of the lighting direction to be near 30 degrees relative to the orthogonal axis.

12. The method according to claim 1 including arranging the light source to comprise a single common light generating device which is arranged to selectively communicate with each one of the four lighting positions.

13. The method according to claim 1 including providing a computer device to calculate the surface gradient using the images and storing the surface gradient once calculated.

14. The method according to claim 1 including providing a computer device to calculate the surface gradient using the images and displaying the surface gradient once calculated.

15. The method according to claim 1 including determining if a shadow condition exists in one of the four images by comparing intensities of the images to a prescribed threshold, and if a shadow condition exists: i) determining three images of the four images which are least affected by shadow; and ii) determining a surface gradient of the surface using the three images.

16. The method according to claim 15 including arranging the prescribed threshold to comprise a percentage of a maximum intensity among the intensities of the images and determining if the shadow condition exists if intensity of one of the images is less than the prescribed threshold.

17. The method according to claim 16 wherein the prescribed threshold is approximately 4% of the maximum intensity among the intensities of the images.

18. The method according to claim 15 including, if no shadow condition exists and no specularity condition exists, determining a surface gradient of the surface using all four of the images.

19. The method according to claim 15 including determining three images of the four images which are least affected by shadow by excluding the image having lowest intensity.

20. A method of evaluating texture of a surface, the method comprising:

providing an image capturing device arranged to capture an image;

providing a source of light arranged to project light in a lighting direction;

locating the image capturing device along an orthogonal axis extending perpendicularly from the surface and facing the surface in a direction of the orthogonal axis so as to be arranged to capture an image of the surface;

sequentially projecting light onto the surface from each of four light source positions spaced circumferentially about the orthogonal axis;

arranging the lighting direction to be at a constant angle of inclination relative to the orthogonal axis in each of the four light source positions;

arranging an intensity of the projected light to be constant in each of the four light source positions;

capturing four images of the surface using the image capturing device in which the surface is illuminated by the light source from a respective one of the four lighting positions when each of the four images are captured;

including:

determining if a shadow condition exists in one of the four images by comparing intensities of the images to a prescribed threshold; and if a shadow condition exists:
i) determining three images of the four images which are least affected by shadow; and
ii) determining a surface gradient of the surface using the three images.

* * * * *